US010776921B2

United States Patent
Kitamura et al.

(10) Patent No.: US 10,776,921 B2
(45) Date of Patent: Sep. 15, 2020

(54) IMAGE PROCESSING APPARATUS, OPERATION METHOD FOR IMAGE PROCESSING APPARATUS, AND RECORDING MEDIUM

(71) Applicant: OLYMPUS CORPORATION, Tokyo (JP)

(72) Inventors: Makoto Kitamura, Hachioji (JP); Mitsutaka Kimura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 102 days.

(21) Appl. No.: 16/193,057

(22) Filed: Nov. 16, 2018

(65) Prior Publication Data
US 2019/0087959 A1    Mar. 21, 2019

Related U.S. Application Data

(63) Continuation of application No. PCT/JP2016/064933, filed on May 19, 2016.

(51) Int. Cl.
*G06T 7/00* (2017.01)
*G06T 7/73* (2017.01)
(Continued)

(52) U.S. Cl.
CPC .......... *G06T 7/0016* (2013.01); *A61B 1/0002* (2013.01); *A61B 1/00045* (2013.01);
(Continued)

(58) Field of Classification Search
CPC ... G06T 7/0012; G06T 7/0014; G06T 7/0016; G06T 7/73; G06T 7/74;
(Continued)

(56) References Cited

U.S. PATENT DOCUMENTS

2007/0195165 A1    8/2007    Hirakawa
2008/0039692 A1    2/2008    Hirakawa
(Continued)

FOREIGN PATENT DOCUMENTS

JP    2006320650 A    11/2006
JP    2006334297 A    12/2006
(Continued)

OTHER PUBLICATIONS

International Search Report dated Aug. 16, 2016 issued in PCT/JP2016/064933.

*Primary Examiner* — Andrew W Johns
(74) *Attorney, Agent, or Firm* — Scully, Scott, Murphy & Presser, P.C.

(57) ABSTRACT

An image processing apparatus including: a memory to store intraluminal images captured by a medical device inserted into a living body, the intraluminal images being associated with time series; and a processor to detect an abnormal area from intraluminal images captured by a medical device inserted into a living body, set a similar abnormal section where the abnormal areas being similar to each other are included, generate information related to the similar abnormal section, extract an intraluminal image that is used as a representative image from among the intraluminal images belonging to the similar abnormal section, control the display device to display the representative image, extract, as the information related to the similar abnormal section from among the intraluminal images, non-representative images which are part of intraluminal images other than the representative image, and control a display device to display the information related to the similar abnormal section.

12 Claims, 12 Drawing Sheets

(51) Int. Cl.
  *G06T 7/60* (2017.01)
  *G06T 7/90* (2017.01)
  *G06T 7/246* (2017.01)
  *A61B 1/00* (2006.01)
  *A61B 1/04* (2006.01)

(52) U.S. Cl.
  CPC .............. *A61B 1/041* (2013.01); *G06T 7/248* (2017.01); *G06T 7/60* (2013.01); *G06T 7/73* (2017.01); *G06T 7/90* (2017.01); *G06T 2207/10016* (2013.01); *G06T 2207/10024* (2013.01); *G06T 2207/10068* (2013.01); *G06T 2207/30028* (2013.01); *G06T 2207/30032* (2013.01); *G06T 2207/30092* (2013.01); *G06T 2207/30096* (2013.01)

(58) Field of Classification Search
  CPC . G06T 2207/30028; G06T 2207/30032; G06T 2207/30092; G06T 2207/30096; A61B 1/00009; A61B 1/00045; A61B 1/0005
  See application file for complete search history.

(56) References Cited

U.S. PATENT DOCUMENTS

| | | |
|---|---|---|
| 2008/0212881 A1 | 9/2008 | Hirakawa |
| 2010/0061597 A1 | 3/2010 | Kanda et al. |
| 2014/0303435 A1 | 10/2014 | Taniguchi |

FOREIGN PATENT DOCUMENTS

| | | |
|---|---|---|
| JP | 2008061704 A | 3/2008 |
| JP | 2009028407 A | 2/2009 |
| JP | 2011024727 A | 2/2011 |
| JP | 5568196 B1 | 8/2014 |
| JP | 2016063868 A | 4/2016 |

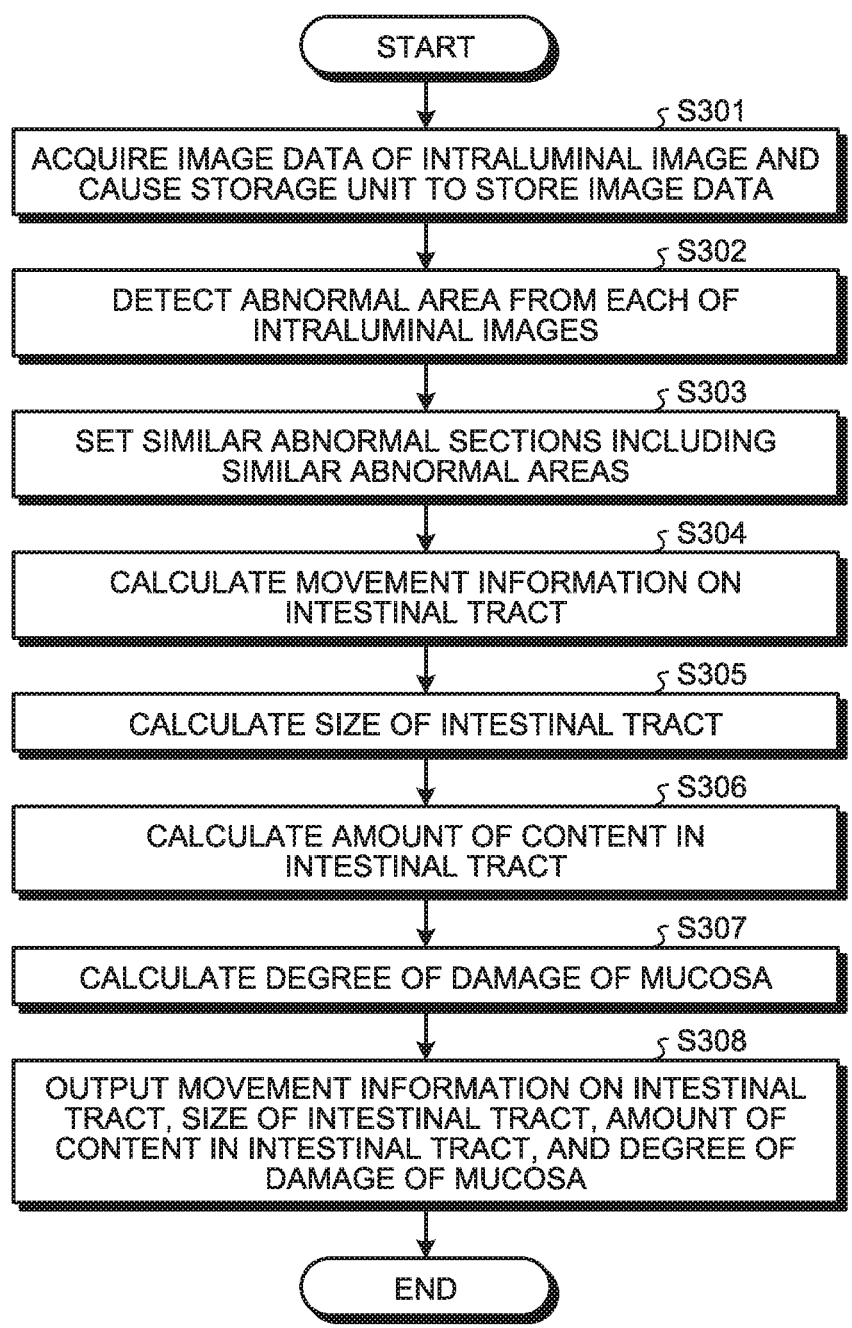

IMAGE PROCESSING APPARATUS, OPERATION METHOD FOR IMAGE PROCESSING APPARATUS, AND RECORDING MEDIUM

CROSS-REFERENCE TO RELATED APPLICATION

This application is a continuation of International Application No. PCT/JP2016/064933, filed on May 19, 2016, the entire contents of which are incorporated herein by reference.

BACKGROUND

The present disclosure relates to an image processing apparatus that detects abnormal areas from luminal images acquired by sequentially capturing the interior of a lumen of, for example, a living body and that causes a display unit to display information calculated based on the detected abnormal areas and relates to an operation method for the image processing apparatus and a recording medium recording a program for operating the image processing apparatus.

There is a known technology for extracting, as representative images, images in each of which a region of interest, such as an abnormal area, has been captured from a series of image groups (hereinafter, also referred to as intraluminal image groups) acquired by sequentially capturing the interior of a lumen of a living body in time series by using a medical observation device, such as an endoscope or a capsule endoscope. By observing the representative images extracted from the image groups, it is possible for users, such as doctors, to reduce the load of observing a large amount of images in detail and thus to make accurate and efficient diagnoses.

For example, Japanese Laid-open Patent Publication No. 2011-24727 discloses an image processing apparatus that detects regions of interest from intraluminal image groups that are sequentially acquired in time series, that classifies the regions of interest into groups based on feature data on the detected regions of interest and based on the time series positions of intraluminal images including the regions of interest, that selects a representative area from the regions of interest classified into each group, and that outputs an image including the selected representative area as a representative image.

SUMMARY

An image processing apparatus according to one aspect of the present disclosure includes: a memory configured to store intraluminal images captured by a medical device which is inserted into a living body, the intraluminal images being associated with time series; and a processor configured to detect an abnormal area from individual intraluminal images captured by a medical device which is inserted into a living body, set a similar abnormal section where the abnormal areas being similar to each other are included, generate information related to the similar abnormal section, extract an intraluminal image that is used as a representative image from among the intraluminal images belonging to the similar abnormal section, control the display device to display the representative image, extract, as the information related to the similar abnormal section from among the intraluminal images belonging to the similar abnormal section, non-representative images which are part of intraluminal images other than the representative image, and control a display device to display the information related to the similar abnormal section.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 15 is a flowchart illustrating image processing performed by the image processing apparatus according to the third embodiment.

DETAILED DESCRIPTION

In the following, modes for carrying out the present disclosure (hereinafter, referred to as an "embodiment") will be described.

First Embodiment

Figure 1:
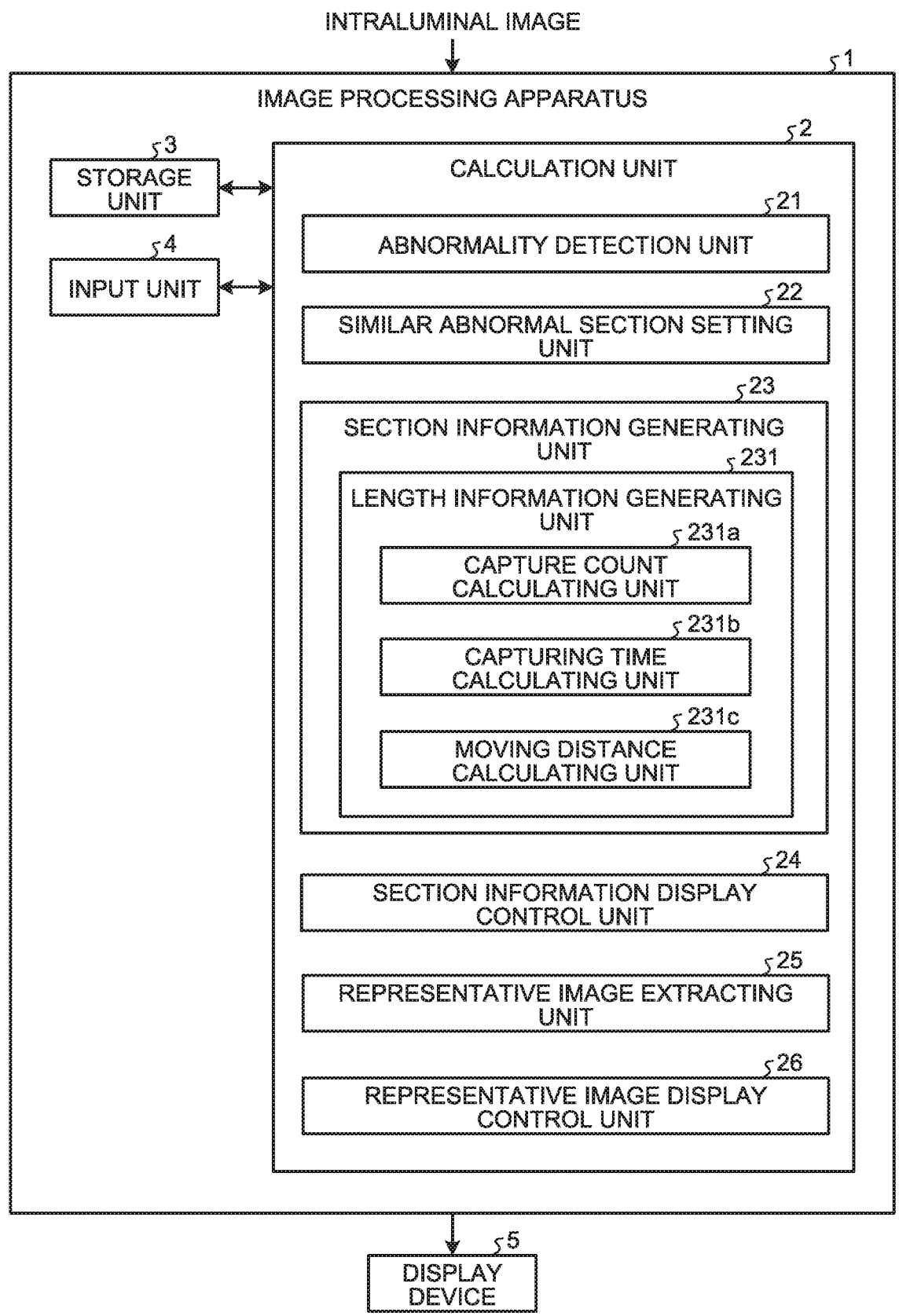
FIG. 1 is a block diagram illustrating a functional configuration of an image processing apparatus according to a first embodiment.

FIG. 1 is a block diagram illustrating a functional configuration of an image processing apparatus according to a first embodiment. An image processing apparatus 1 includes a calculation unit 2, a storage unit 3, and an input unit 4. The image processing apparatus 1 has a function for acquiring intraluminal images captured by a medical device, such as a capsule endoscope or an endoscope and performing predetermined image processing. As the intraluminal images, color images each having pixel levels (pixel values) with respect to wavelength components of R (red), G (green), and B (blue) at corresponding pixel positions are used. The intraluminal images are generated by continuously performing imaging in time series and are sequentially input to the image processing apparatus 1. The image processing apparatus 1 outputs the generated images and information to a display device 5 and causes the display device 5 to display various kinds of information. The display device 5 is implemented by a display device, such as an LCD display or an EL display, and displays various screens including the intraluminal images that have been input from the image processing apparatus 1.

The calculation unit 2 includes an abnormality detection unit 21 that detects an abnormal area of each of intraluminal images that have been continuously captured in time series; a similar abnormal section setting unit 22 that sets a similar abnormal section including the similar abnormal areas; a section information generating unit 23 that calculates section information related to the similar abnormal section; a section information display control unit 24 that outputs the section information calculated by the section information generating unit 23 to the display device 5 and performs control of displaying the section information on the display device 5; a representative image extracting unit 25 that extracts a representative intraluminal image as a representative image from the similar abnormal section; and a representative image display control unit 26 that outputs the representative image extracted by the representative image extracting unit 25 and performs control of displaying the representative image on the display device 5.

The abnormality detection unit 21 detects, based on various kinds of feature data on the intraluminal images, an abnormal area that is a region of interest that is notable in the image. The abnormal area mentioned here is an area in which the properties or the state of a subject in a tract image satisfies a predetermined condition. For example, if a tract image is a tract image (intraluminal image) of a living body, the abnormal area is an area in which the tissue properties of the living body or the state of the interior of the living body satisfy a predetermined condition. More specifically, examples of the area includes an area in which the tissue properties of a living body has been changed, such as an area of an ulcer, an aphtha, erosion, a polyp, a tumor, bleeding, redness, or an abnormality in villus, and an area in which a change in the state, such as bleeding, has occurred in the interior of a living body. In the first embodiment, an example in which an abnormal area is detected based on color feature data (color information) of an intraluminal image will be described. Here, an abnormal area, such as bleeding, redness, or vascular abnormalities, indicates a specific color in red tone and an abnormal area, such as an ulcer or an aphtha, indicates a specific color in white tone. Thus, the abnormality detection unit 21 uses color feature data, such as each of the color components (R component, G component, and B component) of pixel values and the values secondarily calculated based on each of these color components by using a known conversion process (for example, a color difference calculated by using YCbCr conversion, hue and saturation calculated by using HSI conversion, a color ratio of G/R or B/G, etc.), detects an area indicating a specific color included in an intraluminal image, and sets this area to an abnormal area. More specifically, based on the color feature data in various abnormal areas that are previously collected, the abnormality detection unit 21 previously generates an identification reference (color range) of the abnormal areas and records the generated identification reference in the storage unit 3. Then, when detecting an abnormal area from the intraluminal image, the abnormality detection unit 21 reads out this identification reference from the storage unit 3, calculates color feature data of each of the pixels that constitute the intraluminal image, and compares the color feature data of each of the pixels with the identification reference, thereby detecting an abnormal area from the target intraluminal image.

Furthermore, the method of detecting an abnormal area is not limited to the detection method described above. It is possible to use various known methods in which an abnormal area can be detected. For example, a method based on a feature space distance with representative color feature data may also be used. Furthermore, in the description above, the abnormal area has been detected by using color feature data in units of pixels that constitute the intraluminal image. It may also be possible to detect an abnormal area by dividing the intraluminal image into small areas based on edge information or the like on the image and using the color feature data that is in units of small areas. Furthermore, it may also be possible to detect the abnormal area by using shape feature data or texture feature data that are other than the color feature data.

The similar abnormal section setting unit 22 sets, based on the abnormal areas detected by the abnormality detection unit 21, a similar abnormal section that includes the same abnormal area. More specifically, the similar abnormal section setting unit 22 extracts intraluminal images that continue in time series from among the intraluminal images that include the abnormal areas as an intraluminal image group that includes the same abnormal area and sets the intraluminal image group as a single similar abnormal section.

Furthermore, in addition to the extraction method described above, various known methods may be used for the method for extracting the intraluminal image group including the same abnormal area. For example, based on normalized cross-correlation between abnormality images, the amount of change in the motion vector, the amount of change in the pixel value (a luminance value or a G component value), it may also be possible to obtain the amount of change between images and extract an abnormal image group, in which the amount of change is equal to or less than a predetermined value, as an abnormal image group that includes the same abnormal area. Alternatively, it may also be possible to calculate a difference value, between abnormality images, related to shape feature data in the abnormal area (the area, the degree of circularity, etc.) or color feature data (a color ratio, hue, etc.) and extracts an abnormal image group in which the difference value is equal to or less than the previously set predetermined value, as an abnormal image group that includes the same abnormal area.

The section information generating unit 23 includes a length information generating unit 231 that generates length information on a similar abnormal section. The length information generating unit 231 includes a capture count calculating unit 231a that calculates the number of captured images in a similar abnormal section, a capturing time calculating unit 231b that calculates the capturing time of the similar abnormal section, and a moving distance calculating unit 231c that calculates the moving distance of the similar abnormal section. In the first embodiment, the length information generated by the length information generating unit 231 corresponds to information related to the similar abnormal section.

The capture count calculating unit 231a calculates the number of captured images by counting the intraluminal images included in the similar abnormal section.

The capturing time calculating unit 231b calculates the capturing time needed to capture the intraluminal images in the similar abnormal section. This capturing time corresponds to the moving time of the imaging unit in a medical device in the similar abnormal section.

The moving distance calculating unit 231c calculates the moving distance of the medical device in the similar abnormal section. Specifically, the moving distance calculating unit 231c uses a method for calculating a motion vector by performing template matching disclosed in, for example, Japanese Laid-open Patent Publication No. 2006-334297, and estimating the moving distance from this motion vector. Furthermore, the moving distance calculating unit 231c may also calculate the moving distance from an estimation result by using a method of estimating an in-vivo position based on a reception state of radio waves or a detection result of a sensor or the like in the medical device. The method of estimating the in-vivo position is used to calculate the moving distance by estimating the in-vivo positions of the start position and the end position of the similar abnormal section and by calculating the difference between these positions.

If a representative image has been selected via the input unit 4, the section information display control unit 24 refers to the storage unit 3. Then, regarding the similar abnormal section associated with the selected representative image, the section information display control unit 24 acquires the number of captured images, the capturing time, and the moving distance, which are length information generated by the capture count calculating unit 231a, the capturing time calculating unit 231b, and the moving distance calculating unit 231c, respectively, and outputs the information to the display device 5.

The representative image extracting unit 25 extracts, from the intraluminal images that include the abnormal areas detected by the abnormality detection unit 21, an intraluminal image group that includes the same abnormal area and then extracts, from the extracted intraluminal image group, a representative image based on at least one of the degree of importance of each of the abnormal areas and the visibility of each of the abnormal areas. The representative image extracting unit 25 extracts, as a representative image from each of the intraluminal image groups each of which includes the same abnormal area, an intraluminal image that includes an abnormal area in which the degree of importance is high or an intraluminal image in which the visibility of the abnormal area is good. Here, the degree of importance of an abnormal area indicates the correlation between the detection target for a diagnosis made with respect to the intraluminal image and each of the abnormal areas, in other words, indicates a possibility of the detection target, and the degree of importance is determined to be higher (high possibility of the detection target) as the correlation is stronger. For example, if a bleeding source is set to the detection target, the degree of importance of that abnormal area is higher as the detected abnormal area is more likely to be a bleeding source. The representative image display control unit 26 extracts, if a single similar abnormal section is set, at least a single representative image from that similar abnormal section and extracts, if a plurality of different similar abnormal sections is set, at least a single representative image from each of the similar abnormal sections.

A method for extracting a representative image is not particularly limited. For example, the top of the intraluminal images that are arranged in time series in each of the intraluminal image groups may also be extracted as a representative image. Alternatively, an intraluminal image may also be extracted based on color feature data in the same abnormal area included in each of the intraluminal image groups. Specifically, if an abnormal area indicates a specific color in red tone, the intraluminal image that includes a reddish abnormal area is extracted as a representative image with priority, whereas, if an abnormal area indicates a specific color in white tone, the intraluminal image that includes a whitish abnormal area is extracted as a representative image with priority. Furthermore, it may also be possible to extract, as a representative image with priority, the intraluminal image that includes a large abnormal area or the intraluminal image in which the position of an abnormal area is close to the center.

The representative image display control unit 26 outputs the representative image extracted by the representative image extracting unit 25 to the display device 5 that is externally arranged and causes the display device 5 to display the output representative image.

The calculation unit 2 is implemented by using a general-purpose processor, such as a central processing unit (CPU), or a dedicated integrated circuit, such as an application specific integrated circuit (ASIC) or a field programmable gate array (FPGA), which have calculation and control functions. If the calculation unit 2 is implemented by a general-purpose processor or an FPGA, the calculation unit 2 reads out, from the storage unit 3, various programs or various kinds of data stored in the storage unit 3, gives an instruction to or transfers data to each of the units constituting the image processing apparatus 1, and performs overall control of the image processing apparatus 1. If the calculation unit 2 is implemented by using an ASIC, the calculation unit 2 may also perform various processes by itself or may also perform various processes by using various kinds of data or the like stored in the storage unit 3.

The storage unit 3 stores various kinds of information needed to process data on intraluminal images targeted for the process. The storage unit 3 is implemented by various IC memories, such as a read only memory (ROM) or a random access memory (RAM), a hard disk that is built in or connected by a data communication terminal, or an information recording device, such as a CD-ROM, and a reading device thereof. In addition to the image data of an intraluminal image acquired by the image processing apparatus 1, the storage unit 3 stores programs that operates the image processing apparatus 1 and that causes the image processing apparatus 1 to perform various functions and also stores data or the like that is used when the program is being executed.

Specifically, the storage unit 3 stores operation programs according to the first embodiment or various parameters that are used when a process of detecting an abnormal area or the like is performed.

The various programs, such as an image processing program, stored in the storage unit 3 may also be recorded in a computer readable recording medium. Furthermore, recording of the various programs into the storage unit 3 or the recording medium may also be performed at the time of shipment of the computer or the recording medium as a product or may also be performed by a download via a communication network. The communication network mentioned here is implemented by, for example, an existing public circuit network, a local area network (LAN), a wide area network (WAN), or the like, irrespective of a wired or wireless manner.

The input unit 4 receives an input of a signal generated in response to an operation performed from the outside and inputs the received signal to the calculation unit 2. Here, the input unit 4 is implemented by using, for example, a user interface, such as a keyboard or a mouse. Furthermore, if the image processing apparatus 1 includes a display unit, it is also possible to arrange a touch panel on the front surface of the display panel and causes the touch panel to function as an input unit.

The image processing apparatus 1 having the configuration described above may also implemented by using a single computer or may also implemented by a plurality of computers. In the latter case, it is also possible for the computers to perform, in cooperation with each other, processes by sending and receiving data via a communication network. Furthermore, the computer mentioned here can be constituted by, for example, a general-purpose personal computer, a server, or the like.

Furthermore, the configuration of the medical device that is used to input an intraluminal image to the image processing apparatus 1 is not particularly in the present disclosure. An example of the medical device includes a capsule endoscope. The capsule endoscope is orally introduced inside the subject, is moved in the interior of the organ (the digestive tract), and is finally discharged outside the subject. During this period of time, the capsule endoscope performs imaging while moving inside the organ by a peristaltic movement of the organ, sequentially generating image signals, and wirelessly transmits the signals to the image processing apparatus 1 or a relay device that relays the signals between the capsule endoscope and the image processing apparatus 1.

Figure 2:
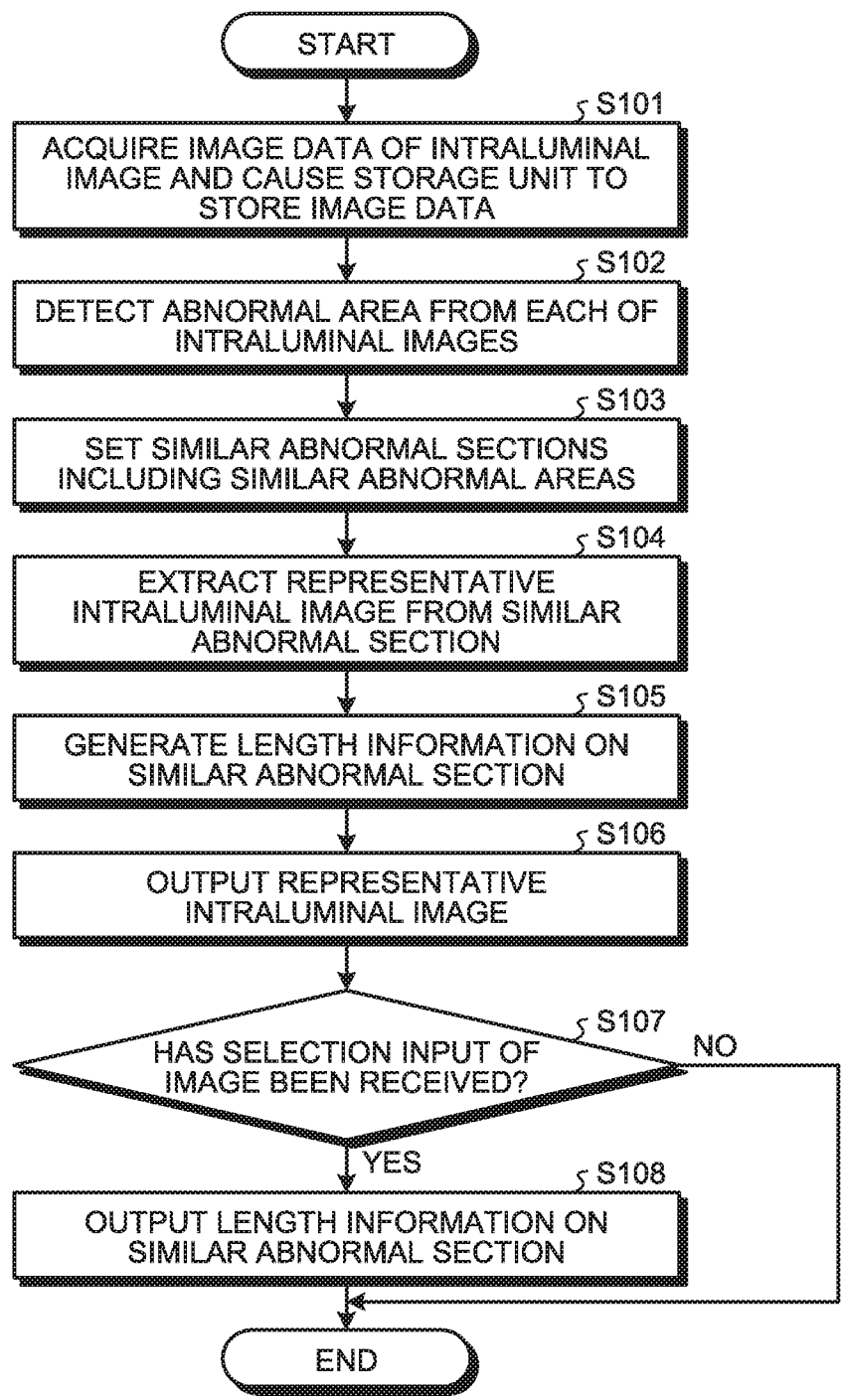
FIG. 2 is a flowchart illustrating image processing performed by the image processing apparatus according to the first embodiment.

In the following, the image processing performed by the calculation unit 2 in the image processing apparatus 1 will be described with reference to FIG. 2 to FIG. 4. FIG. 2 is a flowchart illustrating image processing performed by the image processing apparatus according to the first embodiment. First, if an intraluminal image is input, the image processing apparatus 1 acquires the image data of the intraluminal image and causes the storage unit 3 to write and store the image data (Step S101). A plurality of pieces of the intraluminal image is input in time series. The storage unit 3 stores the input intraluminal images in time series or stores the input intraluminal images associated with time series. The image processing apparatus 1 may also acquire the intraluminal images based on communication with a device, such as a capsule endoscope, that captures the intraluminal images or may also acquire the intraluminal images by reading out the data of the intraluminal images from a recording medium in which the intraluminal images have been recorded.

At subsequent Step S102, the abnormality detection unit 21 performs a process of sequentially reading out image data of the intraluminal images stored in the storage unit 3 and detecting an abnormal area from each of the intraluminal images. Specifically, the abnormality detection unit 21 identifies an abnormal area by reading out the identification reference related to the abnormal area previously recorded in the storage unit 3 and comparing color feature data of each of the pixels constituting the corresponding intraluminal images with the identification reference.

Then, the similar abnormal section setting unit 22 extracts, as a intraluminal image group constituted by a plurality of intraluminal images, the same or a similar abnormal area from the abnormal areas detected at Step S102 and sets the intraluminal image group as a similar abnormal section (Step S103).

At subsequent Step S104, the representative image extracting unit 25, extracts, as a representative image from each of the intraluminal image groups extracted at Step S103, at least one of an intraluminal image that includes an abnormal area in which the degree of importance is high and an intraluminal image that includes an abnormal area in which the visibility is good. The number of representative images to be extracted may also be a predetermined number (for example, a single image from each of the intraluminal image groups) or may also be determined in accordance with the number of intraluminal images belonging to the intraluminal image group (for example, $\alpha$ times as many as the number of intraluminal images, $0<\alpha<1$). In the latter case, if the number of representative images is less than one, at least one representative image is to be extracted. Alternatively, the number of representative images to be extracted is not determined and all of the intraluminal images that satisfy a predetermined reference (for example, the intraluminal images in each of which color feature data is equal to or greater than a predetermined threshold) may also be extracted as the representative images. In a description below, a description will be given with the assumption that, regarding a single similar abnormal section, a single intraluminal image is extracted as a representative image.

At subsequent Step S105, the section information generating unit 23 generates length information on a similar abnormal section. Specifically, the section information generating unit 23 acquires the number of captured images in the similar abnormal section, the capturing time, and the moving distance calculated by the length information generating unit 231 and generates the length information including these pieces of information. After having generated the length information on each of the similar abnormal sections, the section information generating unit 23 causes the storage unit 3 to associate the generated length information with the similar abnormal section and store the associated information.

At subsequent Step S106, the representative image display control unit 26 outputs, to the display device 5 arranged outside, the representative image extracted, at Step S104, by the representative image extracting unit 25 and causes the display device 5 to display the output representative image.

Figure 3:
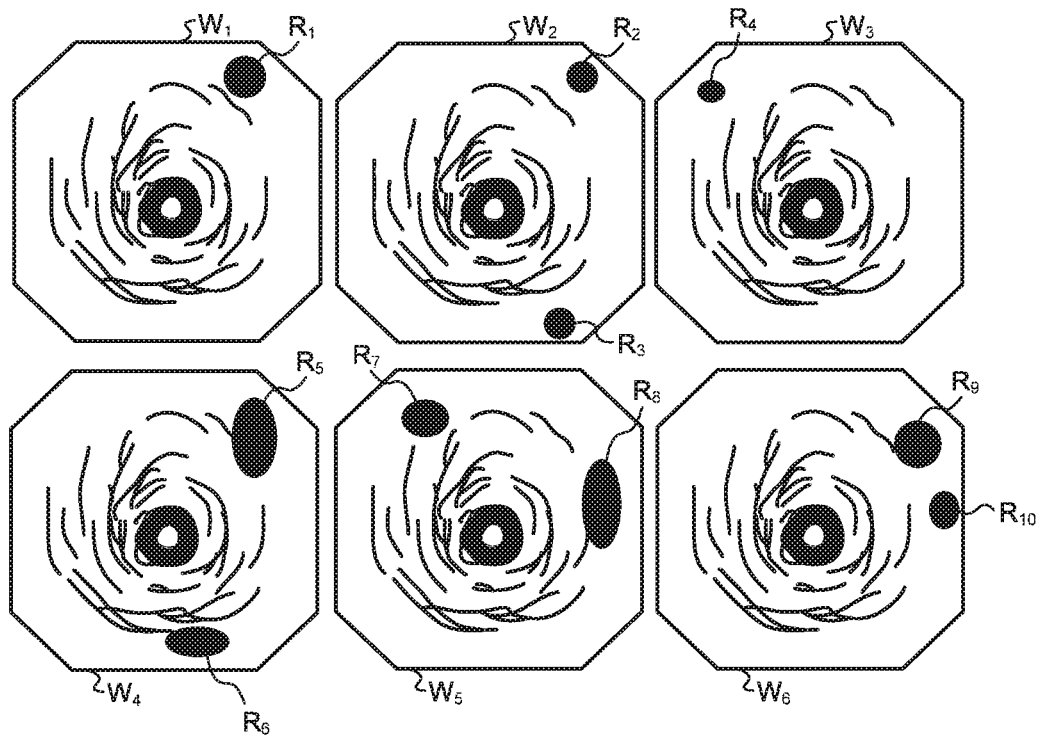
FIG. 3 is a diagram illustrating an example of a display mode of a plurality of representative images extracted in image processing performed by the image processing apparatus according to the first embodiment.

FIG. 3 is a diagram illustrating an example of a display mode of a plurality of representative images extracted in the image processing performed by the image processing apparatus according to the first embodiment. At Step S103, if a plurality of similar abnormal sections is set and a single piece of the representative image is extracted in each of the similar abnormal sections, as illustrated in FIG. 3, representative images $W_1$ to $W_6$ in the corresponding similar abnormal sections are displayed on the display device 5. The representative images $W_1$ to $W_6$ are intraluminal images that include different abnormal areas $R_1$ to $R_{10}$, respectively.

At subsequent Step S107, the calculation unit 2 determines whether a signal that has been received by the input unit 4 and that indicates a selection input, which is used to select one of the plurality of representative images $W_1$ to $W_6$ displayed on the display device 5, has been input. At this time, if the selection input has not been received (No at Step S107), the calculation unit 2 ends the image processing. In contrast, if the selection input has been received (Yes at Step S107), the calculation unit 2 moves to Step S108.

At Step S108, the calculation unit 2 determines the selected representative image based on the input signal and outputs the determination result to the section information display control unit 24. The section information display control unit 24 acquires the length information on the similar abnormal section that is associated with the selected representative image and outputs the length information to the display device 5. Consequently, the length information is displayed on the display device 5 together with the representative image.

Figure 4:
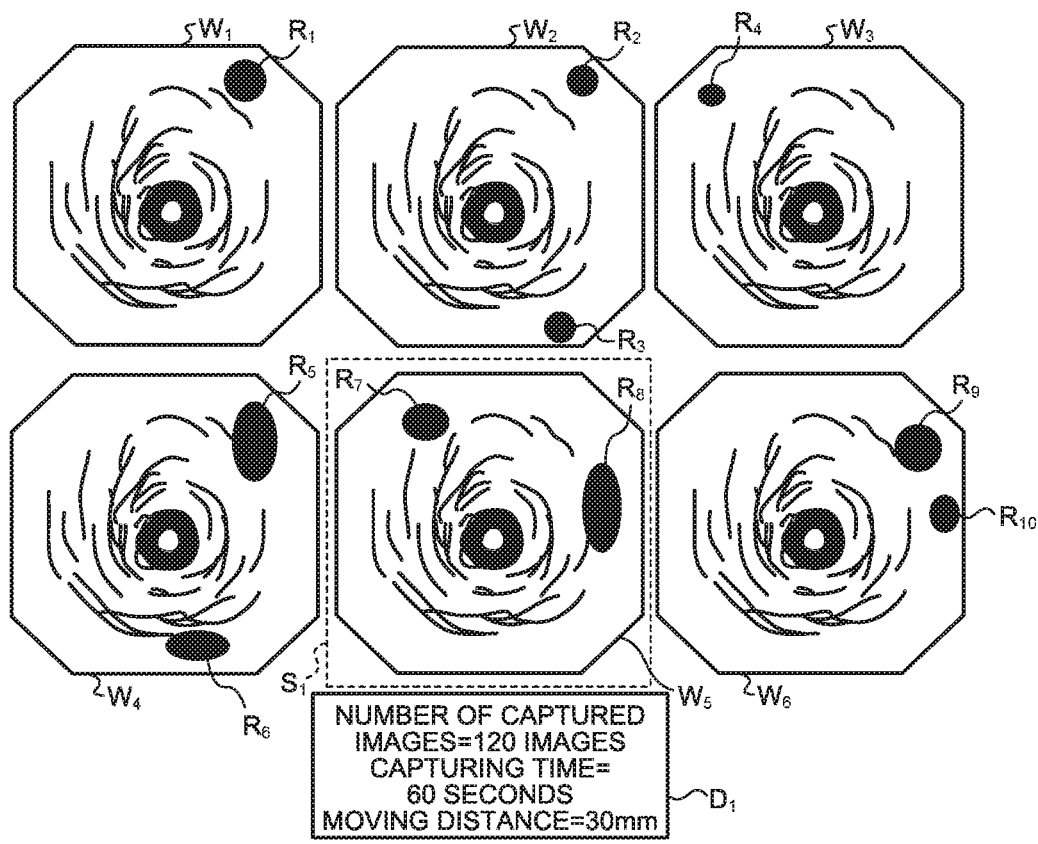
FIG. 4 is a diagram illustrating an example of a display mode in a case where a representative image has been selected from the plurality of representative images extracted in image processing performed by the image processing apparatus according to the first embodiment.

FIG. 4 is a diagram illustrating an example of a display mode in a case where representative images have been selected from the plurality of representative images extracted in the image processing performed by the image processing apparatus according to the first embodiment. If the representative image $W_5$ has been selected via the input unit 4, as illustrated in FIG. 4, a selection frame $S_1$ indicating that the representative image $W_5$ has been selected is displayed and length information $D_1$, which indicates the number of captured images, the capturing time, and the moving distance regarding the similar abnormal section associated with the representative image $W_5$, is displayed. Consequently, a user can check time series information on the selected representative image.

According to the first embodiment described above, regarding the similar abnormal sections that are set by the similar abnormal section setting unit 22, if the section information generating unit 23 generates the number of captured images, the capturing time, and the moving distance as length information and a representative image is selected via the input unit 4, the section information display control unit 24 acquires the length information on the similar abnormal section that is associated with the selected representative image and outputs the length information to the display device 5. Thus, when a representative image is selected from a series of image groups acquired by capturing the interior of a lumen in a living body in time series, it is possible to display time series information related to the region of interest imaged on this representative image. Consequently, by checking the representative image and the time series information related to this representative image, the user can efficiently make a diagnosis with high accuracy.

Furthermore, in the first embodiment described above, a case in which the length information generating unit 231 generates information related to the number of captured images, the capturing time, and the moving distance has been described. It is possible to check time series information on the similar sections to which the representative image belongs as long as at least one piece of information on the number of captured images, the capturing time, and the moving distance is present. Namely, in the configuration used in the first embodiment described above, at least one of the capture count calculating unit 231a, the capturing time calculating unit 231b, and the moving distance calculating unit 231c may be included.

In the first embodiment described above, a case of displaying, if a representative image has been selected, the selection frame $S_1$ illustrated in FIG. 4 and the length information $D_1$ that is associated with this representative image has been described. The embodiment is not limited to this. In the following, in a first to a third modifications, an example of a display, if a representative image has been selected, that is displayed by the display device 5 will be described.

First Modification of First Embodiment

Figure 5:
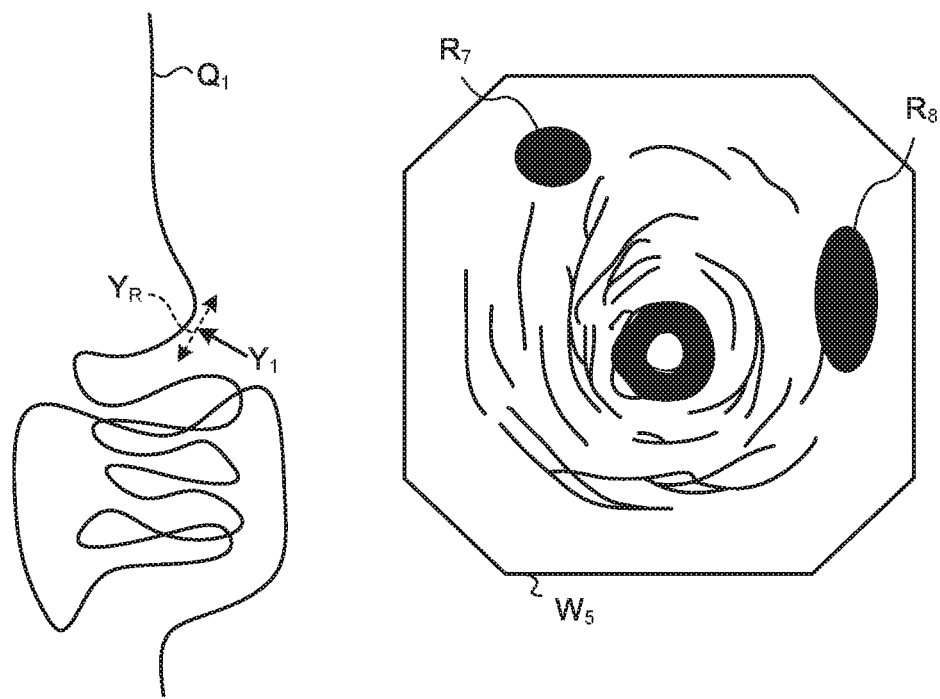
FIG. 5 is a diagram illustrating an example of a display mode in a case where a representative image has been selected from the plurality of representative images obtained in image processing performed by an image processing apparatus according to a first modification of the first embodiment.

In the first modification, an image indicating the position or the like of a medical device in the interior of the body is displayed together with the selected representative image. FIG. 5 is a diagram illustrating an example of a display mode in a case where a representative image has been selected from the plurality of representative images obtained in image processing performed by an image processing apparatus according to a first modification of the first embodiment.

If the representative image $W_5$ has been selected via the input unit 4, at Step S108 described above, the display device 5 displays, as illustrated in FIG. 5, in addition to the selected representative image $W_5$, a trajectory $Q_1$ of a medical device, such as, a capsule endoscope, that passes through the interior of the body. At this time, as the information related to the selected representative image $W_5$, an arrow $Y_1$ that indicates the position of the representative image $W_5$ in the trajectory $Q_1$ and a broken line arrow $Y_R$ that indicates a similar abnormal section to which the representative image $W_5$ belongs are added to the trajectory $Q_1$.

The section information display control unit 24 calculates the display position of the arrow $Y_1$ based on the trajectory information that is associated with the representative image $W_5$. Furthermore, the section information display control unit 24 calculates the number of captured images, the capturing time, and the moving distance that are the length information and that are generated by the capture count calculating unit 231a, the capturing time calculating unit 231b, and the moving distance calculating unit 231c, respectively; calculates the positional information on the capsule endoscope in the interior of the body based on the start position and/or the end position of the similar abnormal section; and integrates the length information with the positional information, thereby generating and outputting the broken line arrow $Y_R$ that is in-vivo position integration information. Furthermore, the display position and the display range of the broken line arrow $Y_R$ may also be calculated based on trajectory information that is associated with each of the intraluminal images at the start position and the end position of the similar abnormal section including the representative image $W_5$.

Second Modification of First Embodiment

Figure 6:
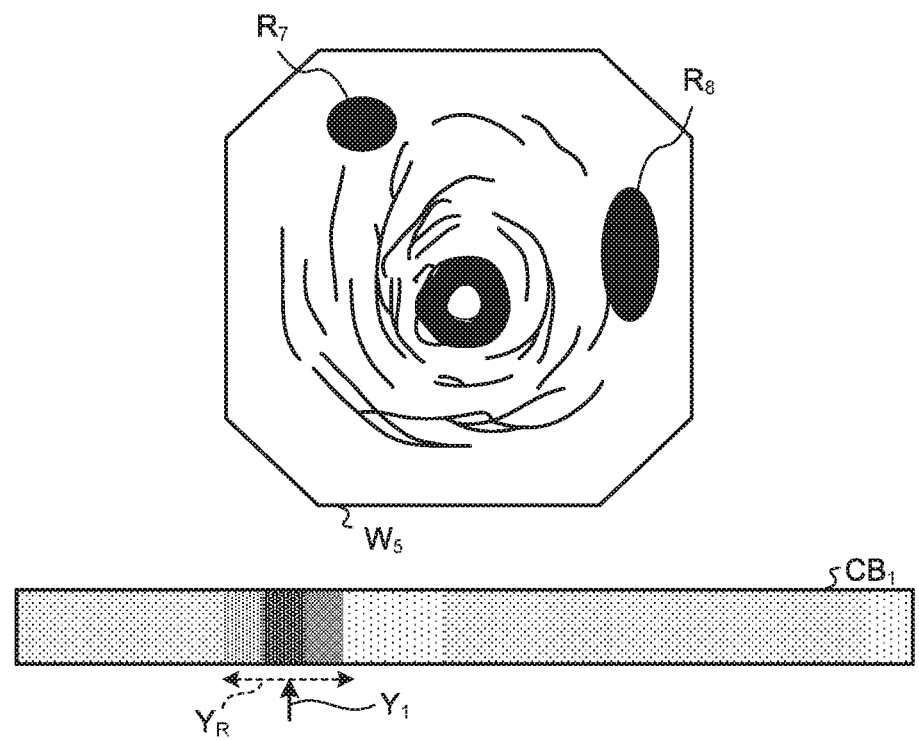
FIG. 6 is a diagram illustrating an example of a display mode in a case where a representative image has been selected from the plurality of representative images obtained in image processing performed by an image processing apparatus according to a second modification of the first embodiment.

In the second modification, an image that indicates the position or the like of the medical device in the interior of the body is displayed together with the selected representative image. FIG. 6 is a diagram illustrating an example of a display mode in a case where a representative image has been selected from the plurality of representative images obtained in image processing performed by an image processing apparatus according to a second modification of the first embodiment.

If the representative image $W_5$ has been selected via the input unit 4, at Step S108 described above, the display device 5 displays, as illustrated in FIG. 6, in addition to the selected representative image $W_5$, a color bar $CB_1$ in which the average colors of the plurality of intraluminal images acquired by the medical device are arranged in time series. At this time, as the information related to the selected representative image $W_5$, the arrow $Y_1$ that indicates the position of the representative image $W_5$ in the color bar $CB_1$ and the broken line arrow $Y_R$ that indicates the similar abnormal section including the representative image $W_5$ are added to the color bar $CB_1$. The section information display control unit 24 calculates the display position of the arrow $Y_1$ based on the position of the average color of the intraluminal image that is the representative image $W_5$. Furthermore, the section information display control unit 24 calculates the display position and the display range of the broken line arrow $Y_R$ based on the position of the average color of each of the intraluminal images at the start position and the end position of the similar abnormal section to which the representative image $W_5$ belongs.

Third Modification of First Embodiment

Figure 7:
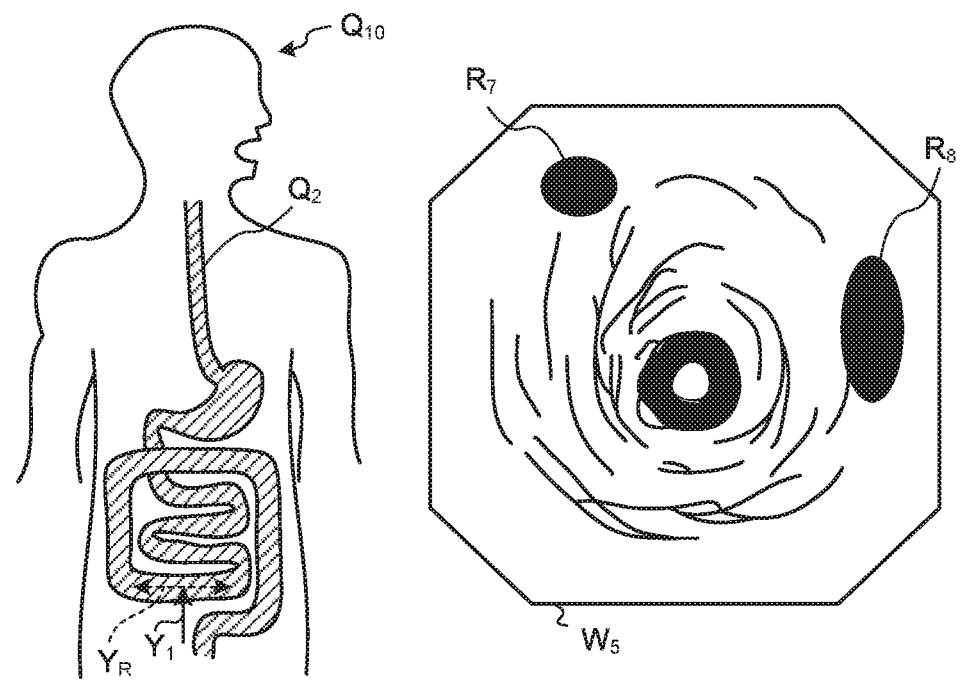
FIG. 7 is a diagram illustrating an example of a display mode in a case where a representative image has been selected from the plurality of representative images obtained in image processing performed by an image processing apparatus according to a third modification of the first embodiment.

In the third modification, an image that indicates the position or the like of the medical device in the interior of the body is displayed together with the selected representative image. FIG. 7 is a diagram illustrating an example of a display mode in a case where a representative image has been selected from the plurality of representative images obtained in image processing performed by an image processing apparatus according to a third modification of the first embodiment of the present invention.

If the representative image $W_5$ has been selected via the input unit 4, at Step S108 described above, the display device 5 displays, as illustrated in FIG. 7, in addition to the selected representative image $W_5$, an organ map $Q_2$ of a subject $Q_{10}$, in the interior of the body, in which a medical device, such as, a capsule endoscope, is introduced. At this time, as the information related to the selected representative image $W_5$, the arrow $Y_1$ that indicates the position of the representative image $W_5$ in the trajectory $Q_1$ and the broken line arrow $Y_R$ that indicates the similar abnormal section including the representative image $W_5$ are added to the organ map $Q_2$. The section information display control unit 24 calculates the display position of the arrow $Y_1$ based on the trajectory information associated with the representative image $W_5$ or based on the moving distance of the capsule endoscope. Furthermore, the section information display control unit 24 calculates the display position and the display range of the broken line arrow $Y_R$ based on the trajectory information and the moving distance that are associated with each of the intraluminal images at the start position and the end position of the similar abnormal section to which the representative image $W_5$ belongs.

Furthermore, in the first to the third modifications described above, the length information $D_1$ according to the first embodiment may also be displayed.

Fourth Modification of First Embodiment

Figure 8:
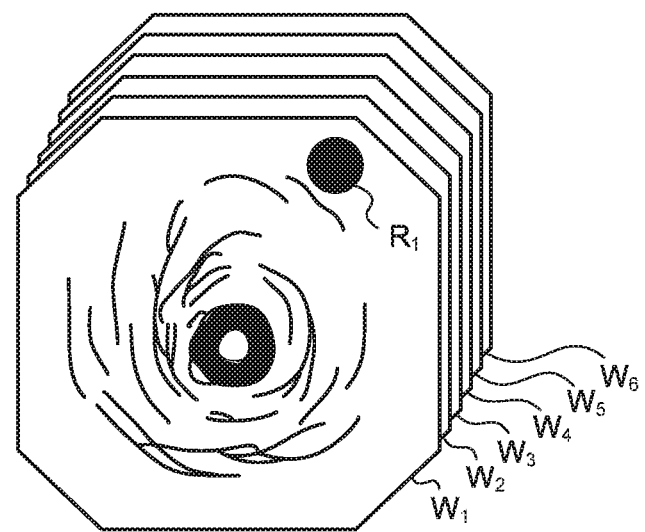
FIG. 8 is a diagram illustrating an example of a display mode of a plurality of representative images extracted in image processing performed by an image processing apparatus according to a fourth modification of the first embodiment.

In the first embodiment described above, a case in which a plurality of extracted representative images are collectively arranged and displayed as still images. In the fourth modification, these images may also be displayed by being changed. FIG. 8 is a diagram illustrating an example of a display mode of a plurality of representative images extracted in image processing performed by an image processing apparatus according to a fourth modification of the first embodiment. As illustrated in FIG. 8, the extracted representative images $W_1$ to $W_6$ are arranged based on a condition that is previously set and are displayed, on the display device 5, in the arranged order. As the condition, for example, a value of the time series or an abnormal area may be used. In this way, it may also be possible to display the plurality of extracted representative images as a moving image. In the fourth modification, if a user operates a selection input with respect to the representative images $W_1$ to $W_6$ that are sequentially displayed by being switched, the representative image that is being displayed at the time of selection input is selected and, regarding the selected representative image, the length information $D_1$ illustrated in FIG. 4 or the like is displayed.

Second Embodiment

Figure 9:
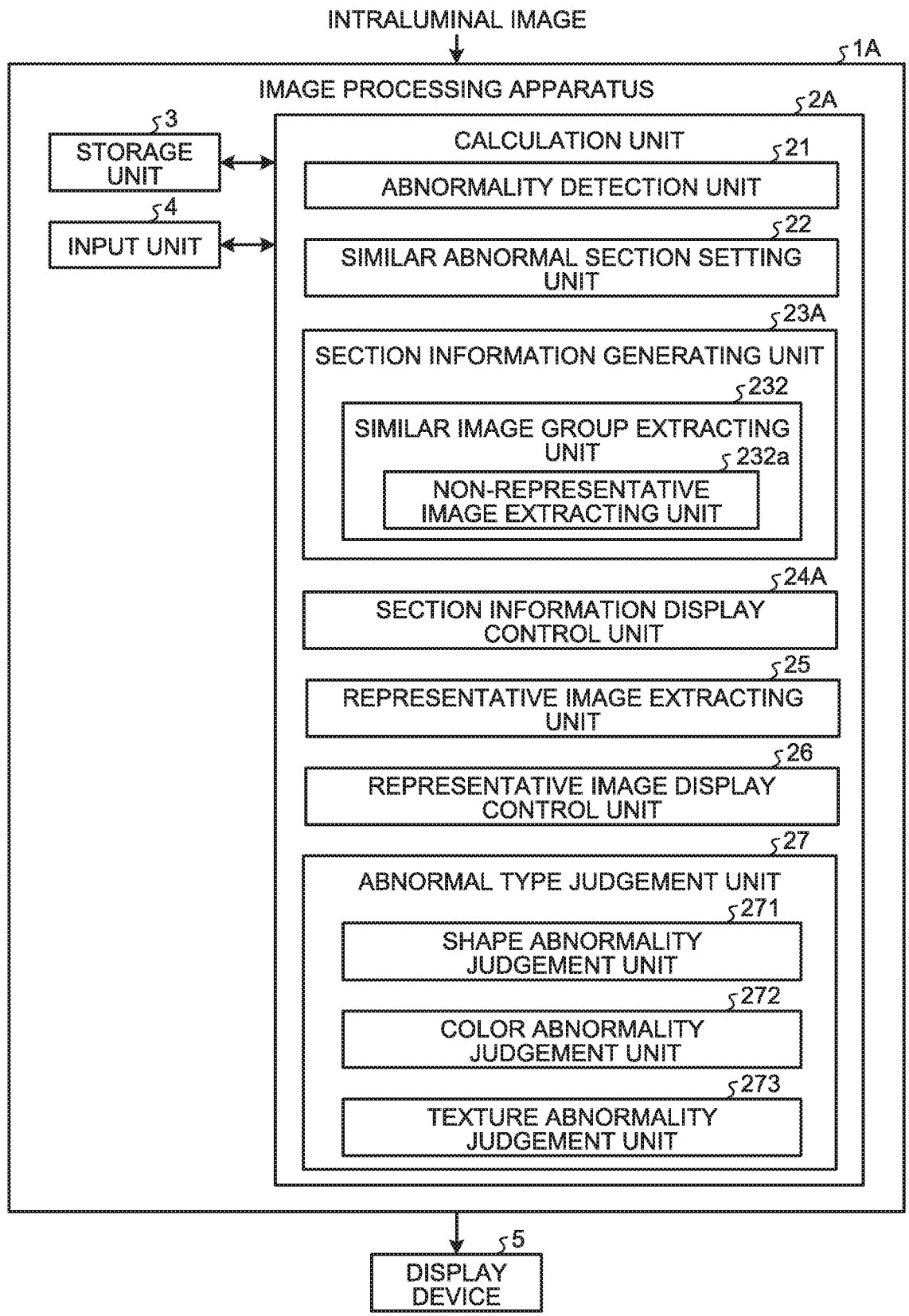
FIG. 9 is a block diagram illustrating a functional configuration of an image processing apparatus according to a second embodiment.

FIG. 9 is a block diagram illustrating a functional configuration of an image processing apparatus according to a second embodiment. An image processing apparatus 1A illustrated in FIG. 9 includes a calculation unit 2A, the storage unit 3, and the input unit 4. In a description below, components that are identical to those included in the calculation unit 2 in the image processing apparatus 1 according to the first embodiment are described by assigning the same reference numerals. The image processing apparatus 1A outputs generated images or information to the display device 5 and causes the display device 5 to display various kinds of information.

The calculation unit 2A includes the abnormality detection unit 21 that detects an abnormal area of each of intraluminal images that have been continuously captured in time series; the similar abnormal section setting unit 22 that sets a similar abnormal section that includes similar abnormal areas; a section information generating unit 23A that calculates information related to the similar abnormal section; a section information display control unit 24A that outputs the section information calculated by the section information generating unit 23A; the representative image extracting unit 25 that extracts a representative intraluminal image as an representative image from the similar abnormal section; the representative image display control unit 26 that outputs the representative image extracted by the representative image extracting unit 25; and an abnormal type judgement unit 27 that judges the type of abnormality.

The section information generating unit 23A includes a similar image group extracting unit 232 that extracts, from among the intraluminal images belonging to the similar abnormal section, an intraluminal image that has not been selected as a representative image. The similar image group extracting unit 232 includes a non-representative image extracting unit 232a that extracts, from the similar abnormal section in time series, all of the intraluminal images belonging to this similar abnormal section. In the second embodiment, the intraluminal image extracted by the similar image group extracting unit 232 corresponds to information related to the similar abnormal section.

The abnormal type judgement unit 27 includes a shape abnormality judgement unit 271 that judges whether an abnormality in shape is indicated, a color abnormality judgement unit 272 that judges whether an abnormality in color is indicated, and a texture abnormality judgement unit 273 that judges whether an abnormality in texture is indicated.

An abnormality in shape of a polyp, a tumor, or the like is usually a circular-shaped area. Thus, the shape abnormality judgement unit 271 judges, based on whether the area has a circular shape, whether the detected abnormal area is an abnormality in shape. Specifically, the shape abnormality judgement unit 271 calculates a gradient intensity of a pixel value (a pixel value of the luminance (Y) component, a pixel value of the G component, etc.) in an intraluminal image by using a known Sobel filter, a known Laplacian filter, or the like. The shape abnormality judgement unit 271 calculates a value of correlation between the gradient intensity calculated by the shape abnormality judgement unit 271 and the circular shape model that has previously been generated and judges, if the value of correlation is equal to or greater than a previously set threshold, that the detection abnormal area is an abnormality in shape. Furthermore, in the second embodiment, a case has been described in which judging whether the detected abnormal area is an abnormality in shape is performed by using pattern matching matched with a previously generated circular shape model. The embodiment is not limited to this. Because only a circular shaped area needs to be detected from an intraluminal image, detection may also be performed by using, for example, the known Hough transformation, RANSAC, Deformable Part Model (DPM), Ellipse and Line Segment Detector (ELSD), etc.

As described above, an aphtha, an ulcer, or the like, which is an abnormality in color, indicates a specific color in white tone, whereas bleeding or redness indicates a specific color in red tone. Thus, the color abnormality judgement unit 272 judges, based on the specific colors in white tone and red tone, whether the detected abnormal area is an abnormality in color. Specifically, the color abnormality judgement unit 272 calculates, from images that have previously collected abnormalities in color and other abnormalities, a pixel value of each of the color components (the R component, the G component, and the B component) and the values, such as a color difference (YCbCr conversion), hue and saturation (HSI conversion), color ratios (G/R and B/G), that are secondarily calculated based on these pixel values by using a known conversion process and sets the judgement standard of an abnormality in color based on the calculated values. Then, based on the color feature data of each of the pixels targeted for the process and based on the previously set judgement standard, the color abnormality judgement unit 272 judges whether each of the pixels is an abnormality in color. Furthermore, in the second embodiment, a case has been described in which an abnormality in color is detected based on the previously set judgement standard. The embodiment is not limited to this. Because only an abnormal area having a specific color needs to be detected from an intraluminal image, an abnormal area may also be detected by using a method performed based on, for example, a feature data space distance with representative color feature data. Furthermore, instead of using color feature data in units of pixels, detecting an abnormal area may also be performed, after having divided an area into small areas based on edge information or the like in an intraluminal image, by judging whether in each of the small areas is an abnormality in color by using color feature data that is used for each small area.

Regarding an abnormality in villus that is an abnormality in texture, the pattern of the front surface of mucosa is usually uneven. Thus, the texture abnormality judgement unit 273 judges an abnormal area in which the pattern of the front surface of mucosa is uneven is an abnormality in texture. Specifically, from previously prepared images each having an abnormality in texture, the texture abnormality judgement unit 273 calculates texture feature data, such as a local binary pattern (LBP) feature data, a distribution of the pixel value of each of the color component (R component, G component, and B component) and decides the judgement standard of an abnormality in texture based on the calculated feature data. Then, based on the calculated texture feature data and the judgement standard described above, the texture abnormality judgement unit 273 judges, for each division area obtained by dividing an intraluminal image into a rectangular shape, whether each of the division areas is an abnormality in texture.

Furthermore, in the second embodiment, a description will be given with the assumption that the judgement result obtained by the shape abnormality judgement unit 271 is different from the judgement results obtained by the color abnormality judgement unit 272 and the texture abnormality judgement unit 273.

The section information display control unit 24A outputs an intraluminal image that has not been selected as a representative image. If the shape abnormality judgement unit 271 judges that the representative image is an abnormality in shape, the section information display control unit 24A causes the display device 5 to display the intraluminal image by using a moving image at a high frame rate. In contrast, if the color abnormality judgement unit 272 judges that the representative image is an abnormality in color, and/or the texture abnormality judgement unit 273 judges that the representative image is an abnormality in texture, the section information display control unit 24A causes the display device 5 to display the intraluminal image by using a still image at a low frame rate (decimated display). Because an abnormality in shape (a tumor) is easily confused with a mucosal fold, the abnormality in shape needs to be minutely checked by using continuous image. In contrast, because an abnormality in color and an abnormality in texture are abnormalities that are easily to make a diagnosis from a still image, the abnormality in color is promptly displayed by using a still image in order to reduce the diagnosis time.

Figure 10:
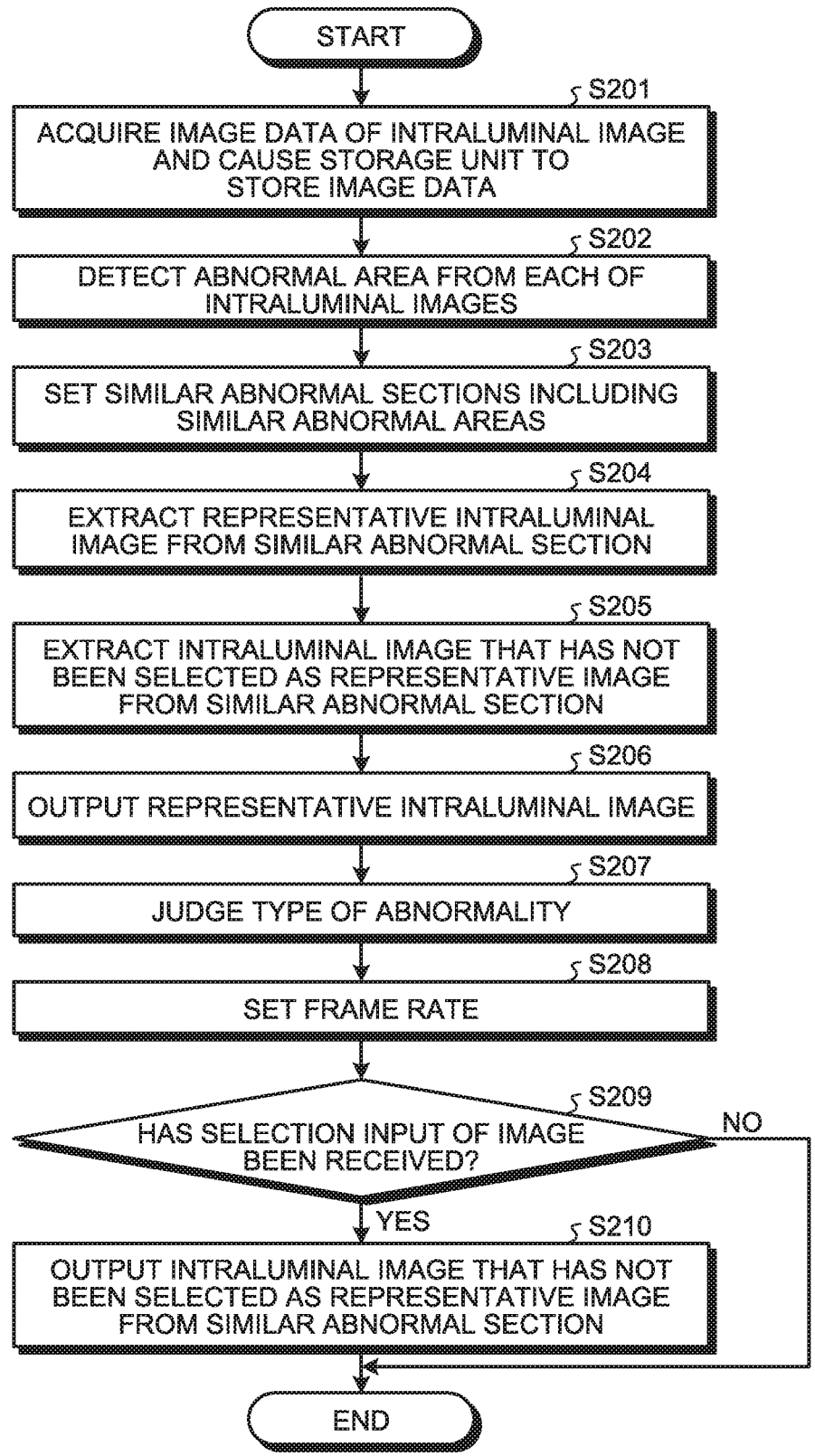
FIG. 10 is a flowchart illustrating image processing performed by the image processing apparatus according to the second embodiment.

In the following, image processing performed by the calculation unit 2A in the image processing apparatus 1A will be described with reference to FIG. 10. FIG. 10 is a flowchart illustrating image processing performed by the image processing apparatus according to the second embodiment. First, if the image processing apparatus 1A receives an input of an intraluminal image, the image processing apparatus 1A acquires image data of the intraluminal image and causes the storage unit 3 to write and store the image data (Step S201). Thereafter, similarly to Steps S102 to S104 in the first embodiment described above, the image processing apparatus 1A detects an abnormal area from each of the intraluminal images (Step S202), sets a similar abnormal section from the detected abnormal area (Step S203), and extracts a representative image from a plurality of intraluminal images belonging to the set similar abnormal section (Step S204).

At subsequent Step S205, the section information generating unit 23A extracts an intraluminal image that has not been selected as a representative image from the similar abnormal section. Specifically, the non-representative image extracting unit 232a extracts an intraluminal image that belongs to the set similar abnormal section. The non-representative image extracting unit 232a may also extract all of the intraluminal images belonging to the similar abnormal section or may also extract intraluminal images at a previously set interval from a plurality of intraluminal images arranged in time series. The section information generating unit 23A outputs the extracted intraluminal images as section information.

At subsequent Step S206, the representative image display control unit 26 outputs the representative image, which has been extracted by the representative image extracting unit 25 at Step S204, to the display device 5 arranged outside and causes the display device 5 to display the output representative image. In the display device 5, for example, as illustrated in FIG. 3, the representative images $W_1$ to $W_6$ in the corresponding similar abnormal sections are displayed on the display device 5.

At subsequent Step S207, the abnormal type judgement unit 27 judges the type of abnormality determining whether the detected abnormal area is an abnormality in shape, an abnormality in color, or an abnormality in texture. Based on each of the judgement results obtained by the shape abnormality judgement unit 271, the color abnormality judgement unit 272, and the texture abnormality judgement unit 273, the abnormal type judgement unit 27 judges the type of abnormality in the abnormal area that is included in the intraluminal image belonging to the set similar abnormal section.

At subsequent Step S208, the section information generating unit 23A sets a frame rate based on the judgement result that is associated with the similar abnormal section. If the shape abnormality judgement unit 271 judges that the representative image is an abnormality in shape, the section information generating unit 23A sets the frame rate of the intraluminal image in the similar abnormal section to which this representative image belongs to a high frame rate. In contrast, if the color abnormality judgement unit 272 judges that the representative image is an abnormality in color, and/or the texture abnormality judgement unit 273 judges that the representative image is an abnormality in texture, the section information generating unit 23A sets the frame rate of the intraluminal image in the similar abnormal section to which this representative image belongs to a low frame rate. If the frame rate is set to be a low frame rate, the plurality of intraluminal images belonging to the similar abnormal section are displayed on the display device 5 in a decimated display mode.

At subsequent Step S209, the calculation unit 2 determines whether a signal that is received from the input unit 4 and that instructs to perform a selection input that select one of the plurality of representative images $W_1$ to $W_6$ displayed on the display device 5 has been input. At this time, if the selection input has not been received (No at Step S209), the calculation unit 2 ends the image processing. In contrast, if the selection input has been received (Yes at Step S209), the calculation unit 2 moves to Step S210.

At Step S210, the calculation unit 2 determines the selected representative image based on the input signal and outputs the determination result to the section information display control unit 24A. The section information display control unit 24A acquires, regarding the similar abnormal section associated with the selected representative image, the intraluminal image extracted by the non-representative image extracting unit 232a and the information on the frame rate related to the similar abnormal section and then outputs the acquired intraluminal image and the information to the display device 5.

According to the second embodiment described above, the abnormal type judgement unit 27 judges the type of abnormality in an abnormal area in the intraluminal image group belonging to the similar abnormal section and the section information generating unit 23A sets the frame rate of the similar abnormal section based on the judgement result obtained by the abnormal type judgement unit 27. If a representative image is selected via the input unit 4, the section information display control unit 24A outputs, to the display device 5, the selected representative image, the intraluminal image other than the representative image extracted by the non-representative image extracting unit 232a, and the frame rate that has been set in the similar abnormal section. Consequently, when a user observes a representative image from a series of image groups acquired by capturing the interior of a lumen in a living body in time series, the user can grasp time series information related to the region of interest imaged on the representative image.

Furthermore, according to the second embodiment, the abnormal type judgement unit 27 judges the type of the abnormal area that is present in the intraluminal image group belonging to the similar abnormal section and the section information generating unit 23A sets the frame rate of the similar abnormal section based on the judgement result obtained by the abnormal type judgement unit 27; therefore, it is possible to change the display mode of the intraluminal image in accordance with the type of abnormality. Consequently, the user can efficiently make a diagnosis with high accuracy.

Furthermore, in the second embodiment described above, a case has been described in which the section information generating unit 23A changes the frame rate in accordance with abnormality in the abnormal area. A display interval of the intraluminal image in a case where the abnormal area is an abnormality in shape may also be set to be shorter than a display interval of the intraluminal image in a case where the abnormal area is an abnormality in color or an abnormality in texture.

Furthermore, in the second embodiment described above, a case has been described in which, regarding all of the similar abnormal sections, the type of abnormality is determined. Regarding only the similar abnormal section to which the selected representative image belongs, the type of abnormality of this similar abnormal section may also be judged. In this case, at Step S207, the abnormal type judgement unit 27 judges the type of abnormality about the similar abnormal section to which the representative image belongs when a representative image is selected at Step S209.

Furthermore, in the second embodiment described above, a case has been described in which the abnormal type judgement unit 27 includes the shape abnormality judgement unit 271, the color abnormality judgement unit 272, and the texture abnormality judgement unit 273 and the frame rate is set based on each of the judgement results. The abnormal type judgement unit 27 may also include one of the shape abnormality judgement unit 271, the color abnormality judgement unit 272, and the texture abnormality judgement unit 273. For example, if the abnormal type judgement unit 27 includes only the shape abnormality judgement unit 271, and, if the shape abnormality judgement unit 271 judges that the abnormal area is an abnormality in shape, the section information generating unit 23A sets the frame rate to a high frame rate, and if the shape abnormality judgement unit 271 judges that the abnormal area is not the abnormality in shape, the section information generating unit 23A sets the frame rate to a low frame rate.

First Modification of Second Embodiment

Figure 11:
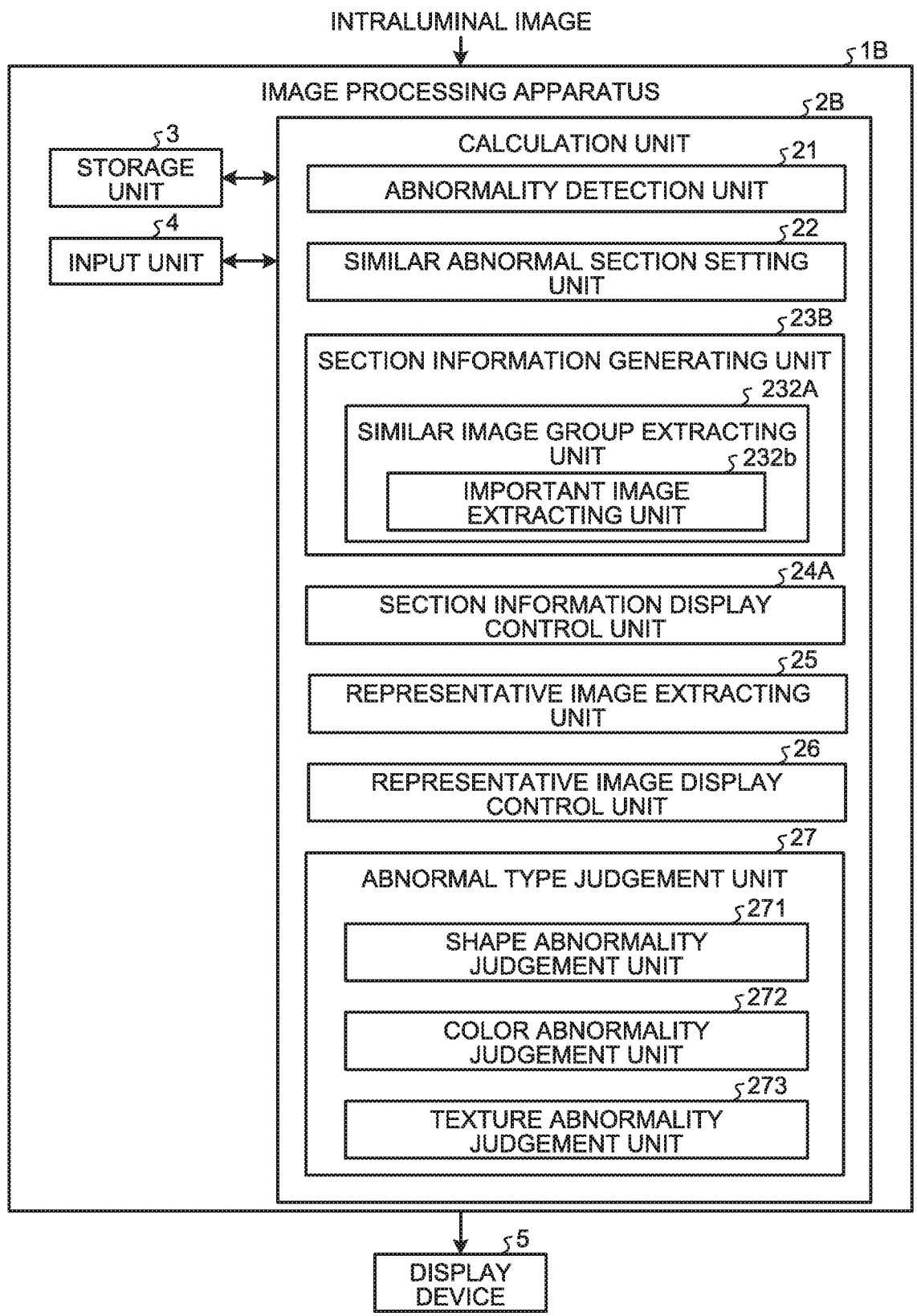
FIG. 11 is a block diagram of a functional configuration of an image processing apparatus according to a first modification of the second embodiment.

FIG. 11 is a block diagram of a functional configuration of an image processing apparatus according to a first modification of the second embodiment. An image processing apparatus 1B illustrated in FIG. 11 includes a calculation unit 2B, the storage unit 3, and the input unit 4. In a description below, components that are identical to those included in the calculation unit 2A in the image processing apparatus 1A according to the second embodiment are described by assigning the same reference numerals. The image processing apparatus 1B outputs generated images or information to the display device 5 and causes the display device 5 to display various kinds of information.

The calculation unit 2B includes the abnormality detection unit 21 that detects an abnormal area of each of intraluminal images that have been continuously captured in time series; the similar abnormal section setting unit 22 that sets a similar abnormal section that includes the similar abnormal areas; a section information generating unit 23B that calculates information related to the similar abnormal section; the section information display control unit 24A that outputs the section information calculated by the section information generating unit 23B; and the abnormal type judgement unit 27 that judges the type of abnormality.

The section information generating unit 23B includes a similar image group extracting unit 232A that extracts an intraluminal image that has not been selected as a representative image from the similar abnormal section. The similar image group extracting unit 232A includes an important image extracting unit 232b that extract, with priority, an important intraluminal image group having a high degree of malignancy from the similar abnormal section. The high degree of malignancy mentioned here is a numerical value that indicates the degree of malignancy of tissue, that is one of indexes that are pathologically set, and that is determined by quantitatively evaluating the degree of malignancy.

The important image extracting unit 232b extracts, with priority, from among a plurality of intraluminal images belonging to the similar abnormal section, an intraluminal image having a high degree of malignancy. Specifically, the important image extracting unit 232b calculates, from previously prepared images having various levels of the degree of malignancy, a pixel value of each of the color components (R component, G component, and B component) and the values, such as a color difference (YCbCr conversion), hue and saturation (HSI conversion), color ratios (G/R and B/G), that are secondarily calculated based on these pixel values by using a known conversion process and sets the identification reference of the degree of malignancy based on the calculated values. The important image extracting unit 232b judges, regarding the intraluminal image belonging to the similar abnormal section, the degree of malignancy based on the previously set judgement standard and extracts, with priority, an intraluminal image having a high degree of malignancy. "Extracting with high priority" mentioned here indicates that the intraluminal images, the number of which has previously been set, are sequentially extracted in the order of intraluminal images having a high degree of malignancy.

According to the first modification, because the important image extracting unit 232b extracts, from among a plurality of intraluminal images belonging to a similar abnormal section, an important intraluminal image having a high degree of malignancy, in addition to the representative image, the intraluminal image that has been judged as having a high degree of malignancy is displayed on the display device 5. Consequently, this makes it possible for a user to make an efficient and reliable diagnosis.

Second Modification of Second Embodiment

Figure 12:
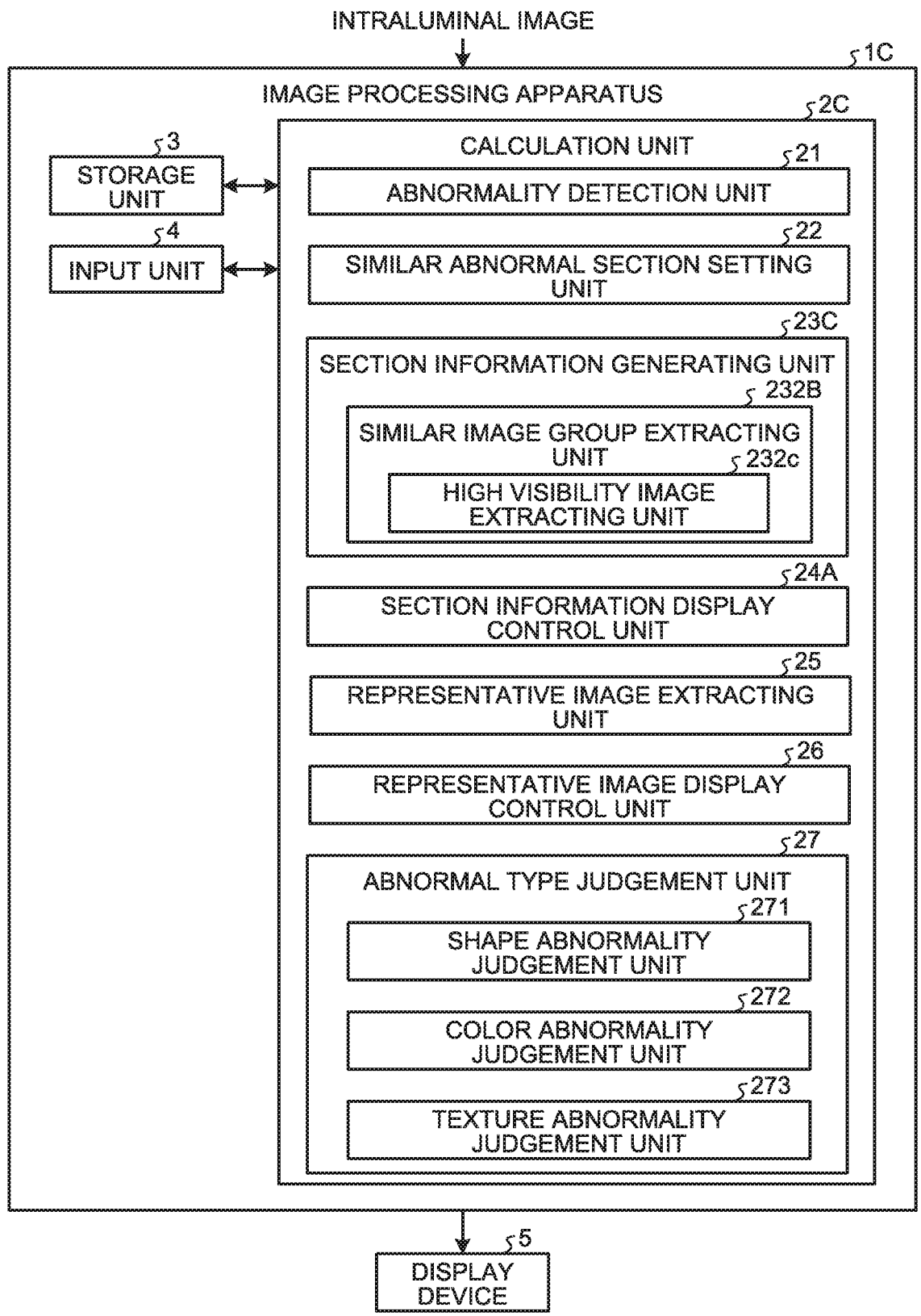
FIG. 12 is a block diagram illustrating a functional configuration of an image processing apparatus according to a second modification of the second embodiment.

FIG. 12 is a block diagram illustrating a functional configuration of an image processing apparatus according to a second modification of the second embodiment. An image processing apparatus 1C illustrated in FIG. 12 includes a calculation unit 2C, the storage unit 3, and the input unit 4. In a description below, components that are identical to those included in the calculation unit 2A in the image processing apparatus 1A according to the second embodiment are described by assigning the same reference numerals. The image processing apparatus 1C outputs generated images or information to the display device 5 and causes the display device 5 to display various kinds of information.

The calculation unit 2C includes the abnormality detection unit 21 that detects an abnormal area of each of intraluminal images that have been continuously captured in time series; the similar abnormal section setting unit 22 that sets a similar abnormal section that includes the similar abnormal areas; a section information generating unit 23C that calculates information related to the similar abnormal section; the section information display control unit 24A that outputs the section information calculated by the section information generating unit 23C; and an abnormal type judgement unit 27 that judges the type of abnormality.

The section information generating unit 23C includes a similar image group extracting unit 232B that extracts an intraluminal image that has not been selected as a representative image from the similar abnormal section. The similar image group extracting unit 232B includes a high visibility image extracting unit 232c that extracts, with priority, an intraluminal image group having high visibility from the similar abnormal section. The visibility mentioned here is a numerical value that indicates the degree of appearance of an object in an image and that is determined by quantitatively evaluating the degree of appearance.

The high visibility image extracting unit 232c extracts, with priority, from among a plurality of intraluminal images belonging to the similar abnormal section, an intraluminal image group in which the visibility is high and a diagnosis can be easily made. Specifically, the high visibility image extracting unit 232c calculates, from previously prepared images having various levels of visibility, a pixel value of each of the color components (R component, G component, and B component) and the values, such as a color difference (YCbCr conversion), hue and saturation (HSI conversion), and color ratios (G/R and B/G), that are secondarily calculated based on these pixel values by using a known conversion process and determines the judgement standard of visibility based on the calculated values. The high visibility image extracting unit 232c judges the visibility of the intraluminal image belonging to the similar abnormal section based on the previously determined judgement standard and extracts, with priority, an intraluminal image with high visibility.

According to the second modification, because the high visibility image extracting unit 232c extracts, from among a plurality of intraluminal images belonging to a similar abnormal section, an intraluminal image with high visibility, the intraluminal image that has been judged to be an image with high visibility is displayed, in addition to the representative image, on the display device 5. Consequently, this makes it possible for a user to check the representative image and an intraluminal image that is different from the representative image and that has high visibility and it is thus possible for the user to make an efficient diagnosis with high accuracy.

Third Modification of Second Embodiment

Figure 13:
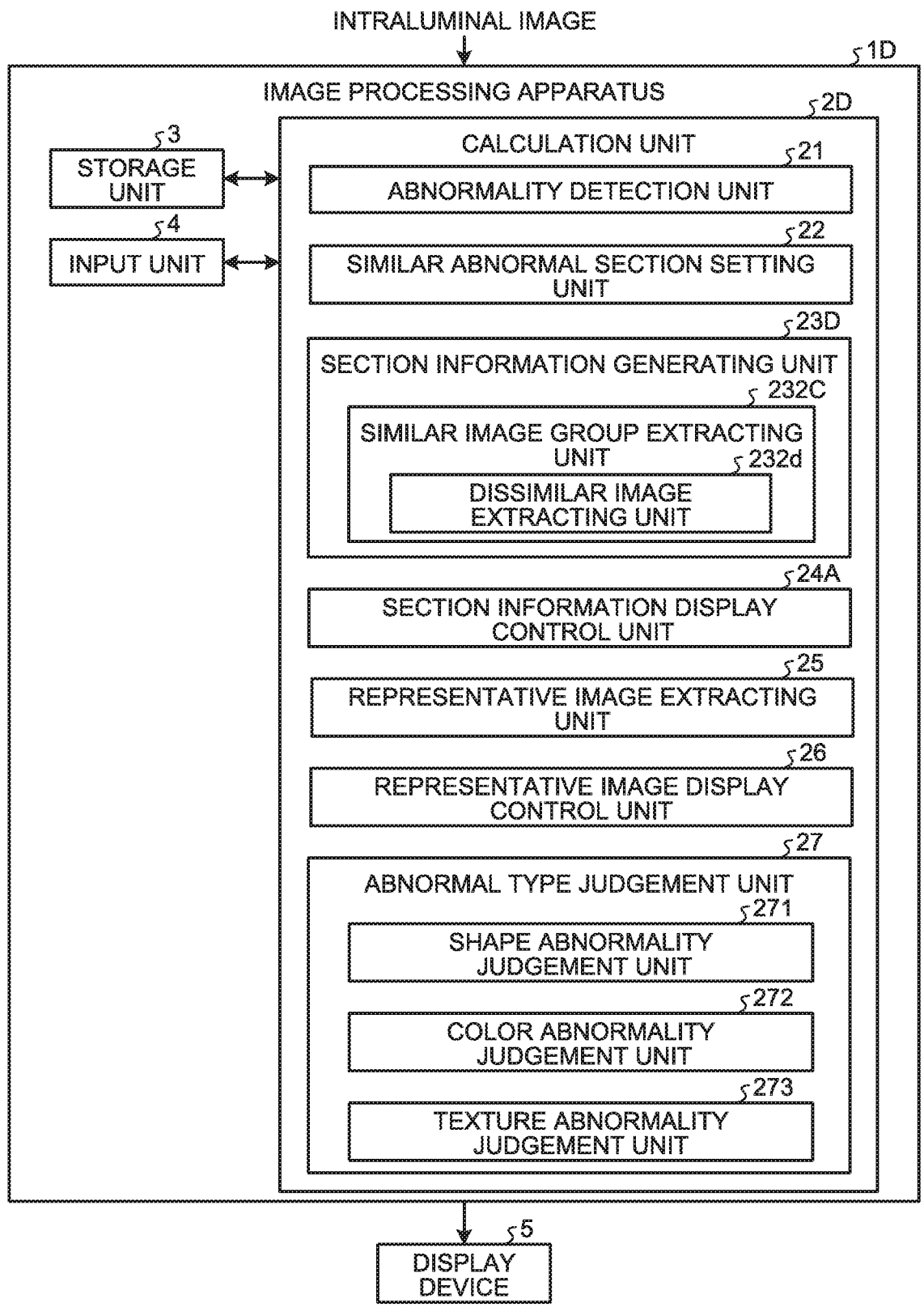
FIG. 13 is a block diagram illustrating a functional configuration of an image processing apparatus according to a third modification of the second embodiment.

FIG. 13 is a block diagram illustrating a functional configuration of an image processing apparatus according to a third modification of the second embodiment. An image processing apparatus 1D illustrated in FIG. 13 includes a calculation unit 2D, the storage unit 3, and the input unit 4. In a description below, components that are identical to those included in the calculation unit 2A in the image processing apparatus 1A according to the second embodiment are described by assigning the same reference numerals. The image processing apparatus 1D outputs generated images or information to the display device 5 and causes the display device 5 to display various kinds of information.

The calculation unit 2D includes the abnormality detection unit 21 that detects an abnormal area of each of intraluminal images that have been continuously captured in time series; the similar abnormal section setting unit 22 that sets a similar abnormal section that includes the similar abnormal areas; a section information generating unit 23D that calculates information related to the similar abnormal section; the section information display control unit 24A that outputs the section information calculated by the section information generating unit 23D; and an abnormal type judgement unit 27 that judges the type of abnormality.

The section information generating unit 23D includes a similar image group extracting unit 232C that extracts an intraluminal image that has not been selected as the representative image from the similar abnormal section. The similar image group extracting unit 232C includes a dissimilar image extracting unit 232d that extracts an intraluminal image group that is not similar to the representative image from the similar abnormal section.

The dissimilar image extracting unit 232d extracts an intraluminal image that is not similar to the representative intraluminal image from the similar abnormal section. Specifically, the dissimilar image extracting unit 232d calculates normalized cross-correlation between the representative image and an intraluminal image that has not been selected as the representative image from the similar abnormal section, an amount of change in motion vector, an amount of change in pixel value (pixel value of the luminance (Y) component, pixel value of the G component, etc.) and extracts, with priority, the intraluminal image having a value in which the calculated amount of change is equal to or greater than a previously set predetermined value. The dissimilar image extracting unit 232d extracts intraluminal images in the order in which, for example, a difference between the amount of change and the predetermined value is greater.

According to the third modification, because the dissimilar image extracting unit 232d extracts, from among a plurality of intraluminal images belonging to the similar abnormal section, an intraluminal image in which the degree of similarity to the representative image is low, an intraluminal image appeared to be different from the representative image is displayed on the display device 5 in addition to the representative image. Consequently, this makes it possible for a user to make an efficient diagnosis with high accuracy.

Furthermore, the section information generating units 23A to 23D according to the second embodiment and the first to the third modifications may also appropriately be combined. Specifically, from among the non-representative image extracting unit 232a, the important image extracting unit 232b, the high visibility image extracting unit 232c, and the dissimilar image extracting unit 232d, at least two units are used in combination and an intraluminal image other than the representative image may be extracted. For example, if the non-representative image extracting unit 232a and the important image extracting unit 232b are used in combination, the important image extracting unit 232b judges the degree of malignancy regarding each of the plurality of intraluminal images extracted by the non-representative image extracting unit 232a and then extracts an intraluminal image that satisfies the judgement standard.

Third Embodiment

Figure 14:
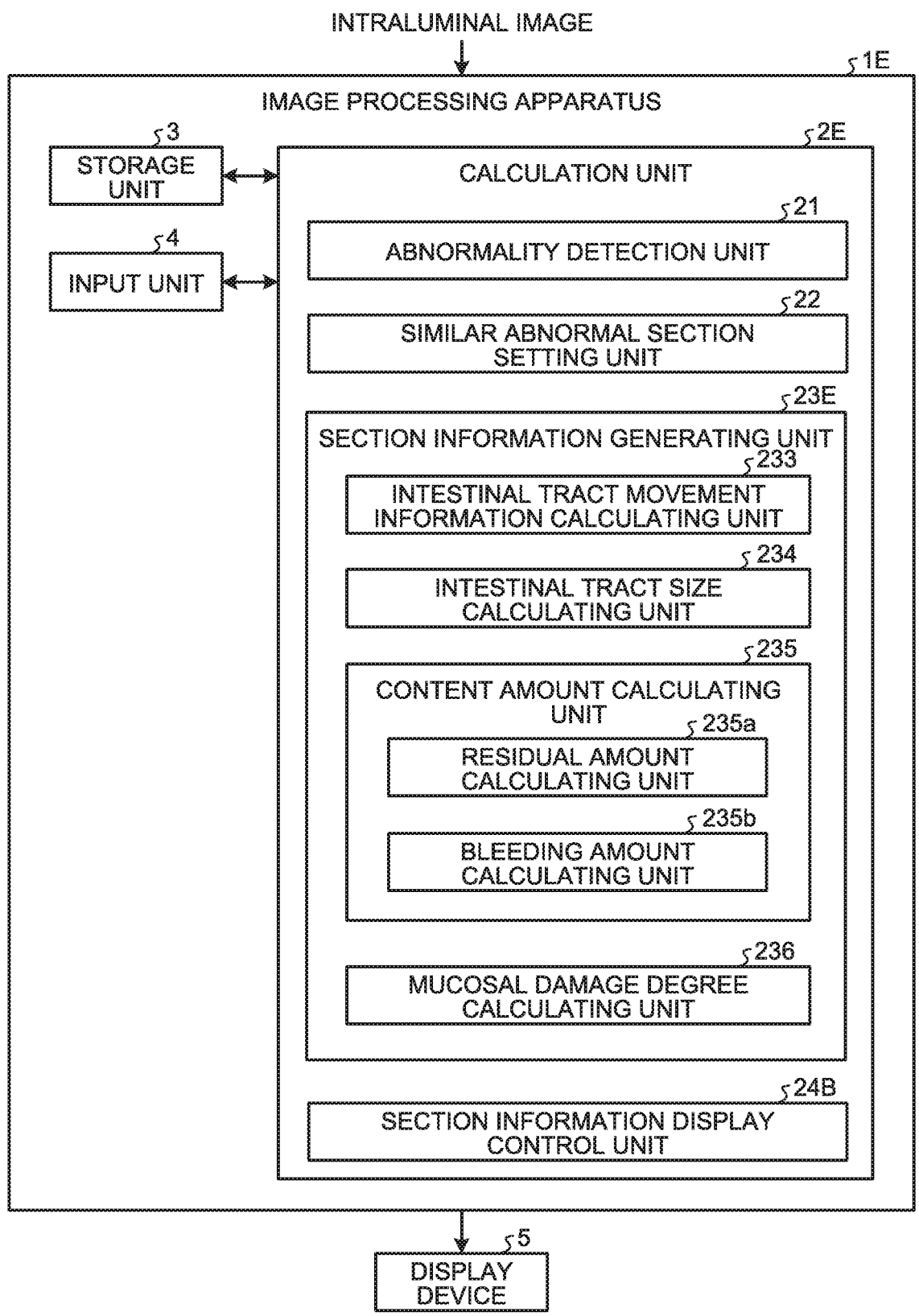
FIG. 14 is a block diagram illustrating a functional configuration of an image processing apparatus according to a third embodiment.

FIG. 14 is a block diagram illustrating a functional configuration of an image processing apparatus according to a third embodiment. An image processing apparatus 1E illustrated in FIG. 14 includes a calculation unit 2E, the storage unit 3, and the input unit 4. In a description below, components that are identical to those included in calculation unit 2 in the image processing apparatus 1 according to the first embodiment are described by assigning the same reference numerals. The image processing apparatus 1E outputs generated images or information to the display device 5 and causes the display device 5 to display various kinds of information.

The calculation unit 2E includes the abnormality detection unit 21 that detects an abnormal area of each of intraluminal images that have been continuously captured in time series; the similar abnormal section setting unit 22 that sets a similar abnormal section that includes the similar abnormal areas; a section information generating unit 23E that generates, as information related to the similar abnormal section, a movement of an intestinal tract in a living body indicated in the similar abnormal section, the size, an amount of content in the intestinal tract, the degree of damage of mucosa; and a section information display control unit 24B that outputs the section information calculated by the section information generating unit 23E. Here, the "content" used in the third embodiment is the residue remaining the intestinal tract or blood. Furthermore, in the third embodiment, the abnormal area detected by the abnormality detection unit 21 indicates an area including the intestinal tract targeted for detection.

The section information generating unit 23E includes an intestinal tract movement information calculating unit 233 that calculates movement information on the intestinal tract; an intestinal tract size calculating unit 234 that calculates the size of the intestinal tract; a content amount calculating unit 235 that calculates an amount of content in the intestinal tract; and a mucosal damage degree calculating unit 236 that calculates the degree of damage of mucosa.

The intestinal tract movement information calculating unit 233 calculates movement information on the intestinal tract. Specifically, the intestinal tract movement information calculating unit 233 calculates information indicating the movement of the intestinal tract based on normalized cross-correlation between the intraluminal image groups in the similar abnormal section, the movement of image calculated by a motion vector, the movement of the medical device, such as a sensor, calculated from the detection result.

The intestinal tract size calculating unit 234 calculates the size of the intestinal tract. Specifically, the intestinal tract size calculating unit 234 calculates the size of the intestinal tract from information on the depth in the interior of an image (a pixel value of the R component, an automatic gain control (AGC) value, etc.) and from the size of an arc area (arc extraction performed based on the Hough transformation).

The content amount calculating unit 235 includes a residual amount calculating unit 235a that calculates an amount of residue and a bleeding amount calculating unit 235b that calculates an amount of bleeding. The residual amount calculating unit 235a and the bleeding amount calculating unit 235b calculates an amount of residue and an amount of bleeding, respectively, in an intraluminal image based on color feature data and texture feature data. The content amount calculating unit 235 may also calculate, in addition to the amounts of residue and bleeding, an amount of bubbles in an intraluminal image.

The mucosal damage degree calculating unit 236 calculates the degree of damage of mucosa. Specifically, the mucosal damage degree calculating unit 236 calculates the degree of damage of mucosa based on presence or absence of a villus or presence or absence of mucosal abnormality detected by image processing. The mucosal damage degree calculating unit 236 calculates the degree of damage of mucosa by comparing an amount of villus per unit area with the judgement standard that is medically set. An amount of villus per unit area can be calculated by extracting a high-frequency component after having performed a frequency analysis on the intraluminal images.

The section information display control unit 24B outputs, for each similar abnormal section to the display device 5 in time series, the movement information on the intestinal tract, the size of the intestinal tract, an amount of content in an abnormal area in the interior of the intestinal tract, and the degree of damage of mucosa that are generated by the section information generating unit 23E.

In the following, image processing performed by the calculation unit 2E in the image processing apparatus 1E will be described with reference to FIG. 15. FIG. 15 is a flowchart illustrating image processing performed by the image processing apparatus according to the third embodiment. First, if an intraluminal image is input, the image processing apparatus 1E acquires image data of the intraluminal image, writes the image data to the storage unit 3, and causes the storage unit 3 to store the image data (Step S301). Thereafter, similarly to Steps S102 and S103 described above in the first embodiment, the image processing apparatus 1E detects an abnormal area from each of the intraluminal images (Step S302) and sets similar abnormal sections from the detected abnormal area (Step S303).

At subsequent Steps S304 to S307, the section information generating unit 23E calculates information related to the intestinal tract for each of the set similar abnormal sections. At Step S304, the intestinal tract movement information calculating unit 233 calculates the movement information on the intestinal tract. At Step S305, the intestinal tract size calculating unit 234 calculates the size of the intestinal tract. At Step S306, the content amount calculating unit 235 calculates an amount of residue and an amount of bleeding. At Step S307, the mucosal damage degree calculating unit 236 calculates the degree of damage of mucosa. The processes performed at Steps S304 to Step S307 do not need to be performed in this order and may also be simultaneously performed as long as these pieces of information can be obtained.

At subsequent Step S308, the section information display control unit 24B acquires information related to the intestinal tract for each similar abnormal section generated by the section information generating unit 23E and outputs the information to the display device 5. The display device 5 displays, for each similar abnormal section, the information on the intestinal tract related to the subject similar abnormal section.

According to the third embodiment, the section information generating unit 23E calculates information on the intestinal tract associated with the similar abnormal section that has been set by the similar abnormal section setting unit 22 and the section information display control unit 24B acquires the information on the intestinal tract generated by the section information generating unit 23E and outputs the information to the display device 5; therefore, when the information on the intestinal tract is displayed from among the series of image groups that have been acquired by capturing the interior of a lumen in a living body in time series, it is possible to display the time series information related to the intestinal tract imaged on the intraluminal images. Consequently, a user can make a diagnosis with high accuracy by checking the time series information related to the intestinal tract imaged on each of the intraluminal images.

Other Embodiments

The embodiments have been described above. The present disclosure is not limited to only the first to the third embodiments described above. For example, by using the first embodiment and the third embodiment in combination, the representative image is displayed together with the information related to the intestinal tract and, if a selection input of the representative image is received, the length information related to the selected representative image may also be displayed. In this way, the present disclosure includes various embodiments or the like that are not described here.

As described above, the image processing apparatus, the operation method for the image processing apparatus, and the program for operating the image processing apparatus according to the present disclosure are useful in efficiently making a diagnosis with high accuracy at the time of diagnosis made by using a series of image groups acquired by capturing the interior of a lumen in a living body in time series.

According to the present disclosure, an advantage is provided in that it is possible to make an efficient diagnosis with high accuracy at the time of diagnosis made by using a series of image groups acquired by capturing the interior of a lumen in a living body in time series.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a processor configured to:
detect an abnormal area from stored individual intraluminal images captured by a medical device which is inserted into a living body, the intraluminal images being associated with time series,
set a similar abnormal section where the abnormal areas being similar to each other are included,
generate information related to the similar abnormal section by extracting, from among the intraluminal images belonging to the similar abnormal section, non-representative images which are part of intraluminal images other than the representative image,
extract an intraluminal image that is used as a representative image from among the intraluminal images belonging to the similar abnormal section,
display the representative image, and
display the information related to the similar abnormal section.

2. The image processing apparatus according to claim 1, wherein the processor extracts all non-representative images including the part of ones from among the intraluminal images belonging to the similar abnormal section.

3. The image processing apparatus according to claim 1, wherein the processor extracts, from among the intraluminal images belonging to the similar abnormal section, intraluminal images each having a high degree of malignancy.

4. The image processing apparatus according to claim 1, wherein the processor extracts, from among the intraluminal images belonging to the similar abnormal section, intraluminal images each having high visibility.

5. The image processing apparatus according to claim 1, wherein the processor extracts, from among the intraluminal images belonging to the similar abnormal section, intraluminal images in each of which a degree of similarity to the intraluminal image that is used as the representative image is relatively low.

6. The image processing apparatus according to claim 1, wherein the processor judges a type of abnormality in the detected abnormal area, and determines a display mode of the intraluminal image based on the type of abnormality.

7. The image processing apparatus according to claim 6, wherein the processor judges, as the type of abnormality in the abnormal area, at least one of an abnormality in shape, color and texture.

8. The image processing apparatus according to claim 7, wherein the processor sets a frame rate of the intraluminal image in a case where the abnormal area is abnormal in shape to be higher than a frame rate of the intraluminal image in a case where the abnormal area is abnormal in color or texture.

9. The image processing apparatus according to claim 7, wherein the processor sets a display interval of the intraluminal image in a case where the abnormal area is abnormal in shape to be shorter than a display interval of the intraluminal image in a case where the abnormal area is abnormal in color or texture.

10. The image processing apparatus according to claim 1, wherein, processor is configured to receive an input indicating an operation of selecting one of the representative images, and the processor displays the information related to the similar abnormal section to which the selected representative image belongs.

11. An operation method for an image processing apparatus, the method comprising:
   detecting an abnormal area from individual intraluminal images captured by a medical device which is inserted into a living body, the intraluminal images being associated with time series;
   setting a similar abnormal section where the abnormal areas being similar to each other are included;
   generating information related to the similar abnormal section by extracting, from among the intraluminal images belonging to the similar abnormal section, non-representative images which are part of intraluminal images other than the representative image;
   extracting an intraluminal image that is used as a representative image from among the intraluminal images belonging to the similar abnormal section; and
   displaying the representative image;
   displaying the information related to the similar abnormal section.

12. A non-transitory computer-readable recording medium on which an executable program is recorded, the program instructing a computer as an image processing apparatus to execute:
   detecting an abnormal area from individual intraluminal images captured by a medical device which is inserted into a living body, the intraluminal images being associated with time series;
   setting a similar abnormal section where the abnormal areas being similar to each other are included;
   generating information related to the similar abnormal section by extracting, from among the intraluminal images belonging to the similar abnormal section, non-representative images which are part of intraluminal images other than the representative image;
   extracting an intraluminal image that is used as a representative image from among the intraluminal images belonging to the similar abnormal section;
   displaying the representative image; and
   displaying the information related to the similar abnormal section.

* * * * *